United States Patent
Buckle et al.

(10) Patent No.: US 6,232,089 B1
(45) Date of Patent: May 15, 2001

(54) CD23 PROCESSING ENZYME PREPARATION

(75) Inventors: Derek Richard Buckle, Redhill; Gary Christie, Berden, both of (GB); Ariane Elizabeth Marolewski, Norwood, MA (US); Ruth Judik Mayer, Wayne, PA (US); David Glynn Smith, Horsham (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/051,529

(22) PCT Filed: Oct. 10, 1996

(86) PCT No.: PCT/US96/16416

§ 371 Date: Aug. 21, 1998

§ 102(e) Date: Aug. 21, 1998

(87) PCT Pub. No.: WO97/13848

PCT Pub. Date: Apr. 17, 1997

Related U.S. Application Data

(60) Provisional application No. 60/005,316, filed on Oct. 10, 1995, and provisional application No. 60/013,427, filed on Mar. 14, 1996.

(51) Int. Cl.$^7$ ................ C12Q 1/37; C12N 9/50
(52) U.S. Cl. ................ 435/23; 435/219; 435/815
(58) Field of Search ................ 435/219, 226, 435/23, 815

(56) References Cited

FOREIGN PATENT DOCUMENTS

WO95/02693    1/1995   (WO) .

OTHER PUBLICATIONS

Okada et al. J. Rheumatol. 14(suppl. 14): 41–2, May 1987.
Kohlman et al. J. Dairy Sci. (1991) 74(12): 4125–36.
Lettellier et al. J. Exp. Med. 172: 693–700, Sep 1990.
Schulz et al. Eur. J. Immunol. (1995) 25: 3191–4.
Letellier et al., Mol. Immunol., 26(12), pp. 1105–1112 (1989).
Schulz et al., Eur. J. Immunol., vol. 25, pp. 3191–3194 (1995).

*Primary Examiner*—Jon P. Weber
*Assistant Examiner*—Michael Meller
(74) *Attorney, Agent, or Firm*—Soma G. Simon; Dara L. Dinner; Charles M. Kinzig

(57) ABSTRACT

The present invention is to the discovery of a novel CD23 processing enzyme which is of importance in the human immune response and regulation of IgE production, and is a protein expressed on the surface of a variety of cells.

16 Claims, 6 Drawing Sheets

CD23 PROCESSING ENZYME PREPARATION

This application is the §371 national stage entry of PCT/US/96/16416, filed Oct. 10, 1996, which is a continuation-in-part application of provisional application U.S. Ser. No. 60/005,316, filed Oct. 10, 1995, and Ser. No. 60/013,427, filed Mar. 14, 1996.

FIELD OF THE INVENTION

This invention relates to processes for identifying and characterizing a novel enzyme. This invention relates to the characterization of a protein expressed on the surface of a variety of cells. The protein is of importance in the human immune response and regulation of IgE production.

BACKGROUND OF THE INVENTION

CD23 (the low affinity IgE receptor, FceRII) is a Type II 45 kDa protein expressed on the surface of various cells, especially mature B-cells, monocytes and macrophages (Delespesse, et al, Adv. Immunol. 49, 149–191 (1991); Gordon, Immun. Today 15, 412–417 (1994)). The structure of CD23, based on its predicted amino acid sequence and homology to other proteins, consists of an N-terminal cytoplasmic domain, a single transmembrane helix, a stalk region and a lectin domain (Ikuta et al, Proc. Nat'l. Acad. Sci. USA 84, 819–823 (1987), Beavil et al, Proc. Nat'l. Acad. Sci. USA 89, 753–757 (1992)). The stalk region is predicted to form a leucine zipper, resulting in oligomerization of CD23 on the cell surface. CD23 expressed on the cell surface is cleaved to soluble forms (sCD23), first identified as IgE binding factors, as these CD23 fragments retain the ability to bind IgE via the lectin domain. The cleavages are known to occur in the stalk region based on the N-terminal sequence of the purified soluble forms of CD23. The two largest fragments begin, respectively, at amino acids 81 and 102 of the human CD23 sequence and are identified as the 37 kDa and 33 kDa soluble CD23 fragments based on their molecular weight as determined by denaturing polyacrylamide electrophoresis; an additional fragment has also been identified as beginning at amino acid 125 with an apparent molecular weight of 29 kDa which is a minor cleavage product (Letellier et al, Molec. Immun. 26, 1105–1112 (1989)).

Additional fragments of CD23 have also been described of apparent molecular weight 25–27 kDa (Bonnefoy et al., Eur. J. Immun. 18, 117–122 (1988); Sarfati et al, Immunology 60, 539–545 (1987)). The 25 kDa fragments correspond to the major form of IgE binding factors found circulating in human serum (Bujanowski-Weber et al., Immunology, 65, 53–58 (1988); Yukawa et al., J. Immun., 8, 2576–2580 (1987)). These smaller fragments are proposed to be derived from the 37, 33 and 29 kDa fragments by an autocatalytic mechanism different from that which produces the larger fragments (Letellier 35 et al, J. Exp. Med. 172, 693–700 (1990)), although this remains unproven. Addition of 10– 20 mM iodoacetamide to cell cultures prevents the accumulation of the 25–27 kDa fragments, but results in the accumulation of 37 and 33 kDa fragments (Letellier et al., J. Immun. 141, 2374–2381 (1988)). Cleavage of CD23 to the larger fragments would then be necessary but not sufficient for production of the 25–27 kDa soluble CD23 fragments. Several reports (Bonnefoy et al., Eur J Immun 18, 117–122 (1988);Sarfati et al, Immunology 60, 539–545 (1987); Moulder et al Eur. J. Immun. 23, 2066–2071 (1993); Bujanowski-Weber et al., Immunology 65, 53–58 (1988)) indicate that under some conditions the 25 kDa fragments accumulate very rapidly in the culture supernatant of CD23-expressing cells, with very little of the larger fragments observed. The cleavage of CD23 from the 37, 33, 29 kDa fragments to the 25–27 kDa fragments may therefore be catalyzed by a different process than that giving rise to the 37, 33 and 29 kDa fragments. The properties of the enzyme responsible for the release of the large soluble CD23 fragments, i.e. the CD23 processing enzyme, have not yet been described.

CD23 has been implicated in human immune response, most clearly in the regulation of IgE production through binding of IgE to CD23 as the low affinity IgE receptor and by immunostimulation via the cytokine activity of the soluble fragments. Particular activities of intact cell-bound CD23 include: a) antigen presentation, b) IgE mediated eosinophil cytotoxicity, c) B cell homing to germinal centres of lymph nodes and spleen, and d) down regulation of IgE synthesis (Delespesse et al, Adv Immunol, 49, 149–191 (1991)). The soluble CD23 fragments (apparent molecular weight 37, 33, 29 and 25 kDa) have multifunctional cytokine properties which appear to play a major role in IgE production. Thus, the excessive formation of soluble CD23 fragments has been implicated in the overproduction of IgE, the hallmark of allergic diseases such as extrinsic asthma, rhinitis, allergic conjunctivitis, eczema, atopic dermatitis and anaphylaxis (Sutton and Gould, Nature, 366, 421428 (1993)). Other biological activities attributed to soluble CD23 fragments include the stimulation of B cell growth and a variety of proinflammatory processes such as the induction of the release of cytokines from monocytes mediated by binding of sCD23 to a receptor (Lecoanet-Henchoz, et al., Immunity 3, 119–125 (1995)). Elevated levels of soluble CD23 have been observed in the serum of patients having B-chronic lymphocytic leukaemia (Sarfati et al, Blood, 71, 94–98 (1988)) and in the synovial fluids of patients with rheumatoid arthritis (Chomarat et al, Arthritis and Rheumatism, 36, 234–242 (1993); Plater-Zyberk and Bonnefoy, Nature Med 1, 781–785 (1995)).

The expression of a CD23 processing enzyme is expected in the many cells which express CD23 in the numerous roles identified for CD23 and the soluble fragments. There exists a need to characterize and purify the CD23 processing enzyme as its importance in the immunologic field is clearly recognised and modulation of its activity will have therapeutic utility.

SUMMARY OF THE INVENTION

The present invention is to the discovery of a novel CD23 processing enzyme preparation. A CD23 processing enzyme preparation, which is a membrane bound preparation, has been found to have the following characteristics:

a) an enzyme activity which produces MW, app 37 and 33 kDa CD23 fragments in the membrane cleavage assay (as described herein);

b) the activity is inhibited by [4-(N-Hydroxyamino)-2-(R)-isobutyl-3-(S)-(2-thiophenethiomethyl)-succinyl]-(S)-phenylalanine-N-methylamide and 1,10-phenanthroline; and c) the activity is not inhibited by the protease inhibitors E-64, PMSF, leupeptin, pepstatin, and TLCK in the membrane assay.

Suitably the preparation also has a pH for optimum activity which is above pH 7.5, and continues to a pH of up to about pH 9.0, and has decreasing activity at a pH below about 7.5.

The novel CD23 processing enzyme preparation may also be characterized by a solubilized preparation which has the following characteristics:
  a) an enzyme activity that produces a MW, app 33 kDa CD23 fragment using the solubilized membrane assay (as described herein);
  b) a pH for optimum activity which is above pH 7.5, and continues to a pH of up to about pH 9.0, and has decreasing activity at a pH below about 7.5;
  c) the activity is inhibited by [4-(N-Hydroxyamino)-2-(R)-isobutyl-3-(S)-(2-thiophenethiomethyl)-succinyl]-(S)-phenylalanine-N-methylamide and 1,10-phenanthroline; and
  d) the activity is not inhibited by the protease inhibitors E-64, PMSF, leupeptin, pepstatin, and TLCK in the membrane assay.

The solubilized preparation may also further have the following characteristics:
  a) an apparent MW by gel filtration, between about 45 to about 60 kDa;
  b) an activity which binds to metal chelating column;
  c) binds to an affinity column made with N-[(3-(S)-propargylthiomethyl-4-(N-Hydroxyamino)-2R-isobutyl)succinyl]-(S)-phenylalanine-N-(6-biotinoyl-aminohexyl)amide and which is eluted by addition of an excess of another CD23 processing inhibitor.

Suitably the metal in the chelating column is a divalent metal, such as Zn, and the column material is preferably a Sepharose based column. Any suitable gel filtration column may be utilized herein, suitably the column is a Superose 12 column, or a Sephacryl S-300 (Pharmacia) column.

Another aspect of the present invention is to a method for preparing purified CD23 processing enzyme preparations. The first of such methods comprise:
  a) preparing purified plasma membranes by aqueous extraction;
  b) solubilizing the membrane proteins, from part (a) with a detergent, such as Nonidet P-40;
  c) applying the solubilized proteins, from part (b), to an anion exchange chromatography column and eluting the CD23 processing activity in the fractions eluting at a salt concentration from about 0.15 to about 0.25 M;
  d) preparing the eluate, from part (c), for gel filtration, and eluting the CD23 processing activity in the fractions with a MW between 45 and 60 kDa;
  e) applying to a immbolizied heparin chromatography column the active fractions from part (d), and eluting the enzyme with a salt gradient, the activity eluting at a salt concentration from about 0.15 to about 0.2 M;
  f) applying to a metal-chelating chromatography column the active fractions from part (e), and eluting the enzyme from the column with 0.1 M imidazole, or other suitable metal ligand, such as a Zn ligand, which eluate has CD23 processing activity upon dilution of the metal ligand, i.e. the imidazole.

Generally the dilution is about a 10 fold dilution. The immbolizied heparin based column is preferably a heparin agarose column. Suitably the metal in the metal chelating column is a divalent metal, such as Zn, and the column material is preferably a Sepharose based column. For the gel filtration column, any suitable column well known to those skilled in the art may be utilized herein. Suitably the column is a Superose 12 column, or a Sephacryl S-300 (Pharmacia) column.

Another process for preparing a purified CD23 processing enzyme preparation comprises:
  a) preparing purified plasma membranes by aqueous extraction;
  b) solubilizing the membrane protein with a detergent, such as Nonidet P-40;
  c) applying the solubilized protein to an affinity column of streptavidin-agarose beads, wherein the affinity column is prepared by first binding to the column a biotinylated CD23 processing inhibitor compound, such as described below in the Synthetic Examples Section, to the streptavidin-agarose beads;
  d) washing the affinity column with buffer, such as binding buffer or binding buffer with NaCl, to remove non-specifically bound proteins,
  e) competing CD23 processing enzyme off the column by addition of an excess of another CD23 processing inhibitor.

The CD23 processing enzyme preparation may be separated from contaminating proteins in either process by using conventional electrophoresis techniques, well known to those skilled in the art.

Another aspect of the present invention is to methods of identifying inhibitors of CD23 processing as described below.

DETAILED DESCRIPTION OF THE DRAWINGS

FIG. 1 depicts a typical time course for production of MW, app 37 and 33 kDa bands from plasma membrane enriched fractions from RPMI 8866 cells.

FIG. 2 demonstrates the inhibition of release of sCD23 from plasma membrane enriched fractions of RPMI 8866 cells by compound 1.

FIG. 3 depicts a typical time course for cleavage of CD23 to MW, app 33 kDa fragment by solubilized RPMI 8866 membrane proteins.

FIG. 4 displays the dependence on CD23 concentration of the production of MW, app 33 kDa sCD23 by solubilized plasma membrane proteins.

FIG. 5a displays a Western blot of CD23 cleaving activity in fractions from a heparin-agarose column of solubilized RPMI 886 membrane proteins.

Figure 8:
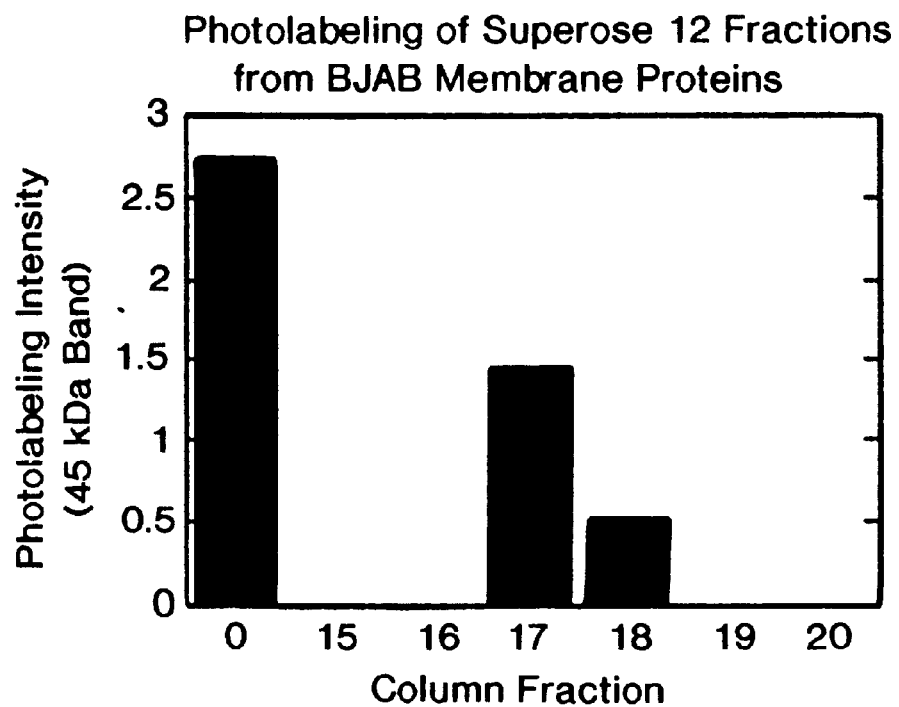

FIG. 8: Photolabeling with compound 3 (Synthetic Example 9) of fractions from Superose 12 column of solubilized BJAB membrane proteins. Fractions were concentrated, photolabeled as described, applied to 12% SDS-PAGE, blotted to PVDF and photolabeled material detected with streptavidin-horseradish peroxidase using ECL methodology. Fraction "0" indicates the photolabeling observed in an unfractionated sample.

Figure 9:
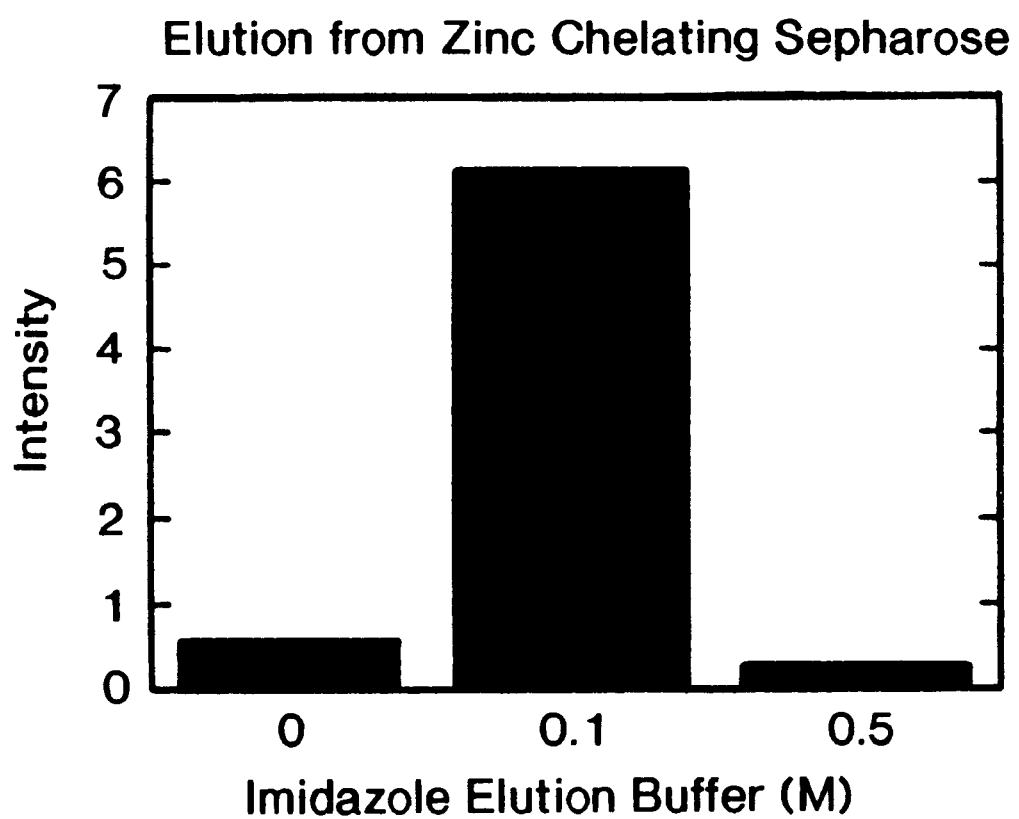

FIG. 9: Elution profile of RPMI 8866 membrane proteins from Zn-chelating Sepharose.

DETAILED DESCRIPTION OF THE INVENTION

Evidence is provided herein that demonstrates the existence of a distinct CD23 processing enzyme whose properties are summarised as follows. The CD23 processing enzyme preparation can be fractionated on a number of suitable chromatographic matrices such as but not limited to Superose 12, Q-Sepharose, or heparin-Sepharose (Pharmacia). The activity can be found in these fractions by assessing the cleavage of exogenous CD23 to the MW, app 33 kDa sCD23 product. The exogenous, purified 45 kDa CD23 incubated without added column fractions does not generate any soluble CD23 fragments. Therefore, this cleavage activity does not reside in the CD23 polypeptide.

The activity which produces the 33 kDa fragment is characterized by inhibition by the metalloprotease inhibitor 1,10-phenanthroline and not by other protease class inhibitors such as trans-epoxysuccinyl-leucylamido-(4-guanidino)-butane (E-64), phenylmethanesulphonylfluoride (PMSF) or pepstatin. The activity is also inhibited by compound 1 ([4-(N-Hydroxyamino)-2-(R)-isobutyl-3-(S)-(2-thiophenethiomethyl)-succinyl]-(S)-phenylalanine-N-methylamide). The pH optimum for activity is above pH 7.5, up to about H 9.0, with decreasing activity below pH 7.5, consistent with a neutral metal-containing protease. The apparent molecular weight (MW) by gel filtration, on a Superose 12 column is from about 45 to about 60 kDa.

By identifying, and characterizing the CD23 processing enzyme it is recognized that one will be able to inhibit this enzymes activity. Such inhibition will have at least a twofold action of a) enhancing negative feedback inhibition of IgE synthesis by maintaining levels of 45 kDa CD23 on the surface of B cells, and b) inhibiting the cytokine activities of the soluble CD23 fragments.

Another aspect of identifying and characterizing the CD23 processing enzyme allows for a method of identifying inhibitors of CD23 processing. Therefore the present invention also relates to novel methods of identifying inhibitors of CD23 processing. One such method comprises:

a) preparing enriched plasma membranes, such as disclosed in Biological Example 1, from cells expressing CD23;

b) incubating the membranes in the presence of an inhibitor; and suitably in the absence of an inhibitor for a control;

c) determining the amount of sCD23 produced by the membrane incubation, such as disclosed in Biological Examples 1, and 2a.

This method further comprises calculation of the IC50 of the inhibitor by reference to the uninhibited membrane cleavage activity (wherein an IC50≦20 uM is considered an active compound), as taught herein. It is possible to differentiate the total amount of sCD23 produced from the relative (or lesser) amount of sCD23 produced which amounts are represented by specific fragments of sCD23, such as the 33 or 37 kDa MW fragments.

Another method for identifying inhibitors of CD23 processing comprises:

a) preparing enriched plasma membranes from cells expressing CD23;

b) incubating the membranes in the presence of, and in the absence of inhibitors (for a control); and c) determining the amount of 33 kDa CD23 produced using a selective antibody such as the 33 kDa fragment, as disclosed in Biological Examples 2 and 2a.

Yet another embodiment of the present invention for identifying inhibitors of CD23 processing comprises:

a) preparing enriched plasma membrane from cells expressing CD23;

b) solublizing the membrane in an appropriate detergent;

c) adding a suitable amount of exogenous, or purified CD23, such as made in Biological Example 2, to the solubilized membrane protein;

d) incubating the mixture of part (c), in the presence of, and in the absence of an inhibitor (as a control);

e) detecting soluble fragments of CD23 using selected antibodies to fragments of CD23, such as disclosed in Biological Examples 2 and 2a; or detecting the amount of unprocessed full length CD23.

While the above noted assays utilize full length CD23, it is recognized that similar assays and methods herein may utilize less than the full length protein.

The following Biological Assays herein will further describe the properties of this novel enzyme. Such examples are for illustrative purposes only and are not to be construed as limiting this invention in any manner.

The membrane CD23 cleavage assay (Biological example 1) directly relates the fragments of CD23 produced from a cell-free enriched plasma membrane preparation to the MW, app 37 and 33 kDa fragments of CD23 produced in the culture media of cells, such as RPMI 8866 cells, at the same time localizing the activity to the plasma membrane fraction of the cell. The membrane assay also allows for the identification of compounds which inhibit the processing of CD23 to soluble fragments.

The solubilized membrane protein CD23 cleavage activity assay (biological example 2) demonstrates enzymatic activity wherein the enzyme is mixed with CD23 substrate to produce the MW, app 33 kDa product in a manner which can be described using classical enzyme characteristics such as pH optimum, apparent KM, etc. Together, these two assays show that at least these two fragments of soluble CD23 are formed by the same enzymatic activity, identified as CD23 processing enzyme.

The CD23 processing enzyme can be purified using conventional chromatographic methods by utilising the solubilized membrane assay to identify the fractions generated by various chromatography's which contain the CD23 processing activity.

BIOLOGICAL EXAMPLES

Biological Example 1

Membrane CD23 cleavage activity assay:

Plasma membranes from RPMI 8866 cells, a human Epstein-Barr virus transformed B-cell (Sarfati et al., Immunology 60 (1987) 539–547), or a similar cell line expressing high levels of CD23 are purified using an aqueous extraction method. Cells resuspended in homogenization buffer (20 mM HEPES pH 7.4, 150 mM NaCl, 1.5 mM MgCl2, 1 mM DTT) are broken by $N_2$ cavitation in a Parr bomb and the plasma membrane fraction mixed with other membranes recovered by centrifugation at 10,000×g. The light pellet is resuspended in 0.2 M potassium phosphate, pH 7.2 using 2 ml per 1–3 g wet cells and the nuclear pellet is discarded. The membranes are further fractionated by partitioning between Dextran 500 (6.4% w/w) and polyethylene glycol (PEG) 5000 (6.4% w/w) at 0.25 M sucrose in a total of 16 g per 10–15 mg membrane proteins (Morre and Morre, BioTechniques 7, 946–957 (1989)). The phases are separated by brief centrifugation at 1000×g and the PEG (upper) phase is collected, diluted 3–5 fold with 20 mM potassium phosphate buffer pH 7.4, and centrifuged at 100,000×g to recover membranes in that phase. The pellet is resuspended in phosphate-buffered saline and consists of 3–4 fold enriched plasma membranes as well as some other cell membranes (e.g. lysosomes, Golgi). The membranes are aliquoted and stored at −80° C. Fractionation at 6.6% Dextran/PEG yields plasma membranes enriched 10-fold.

Figure 1:
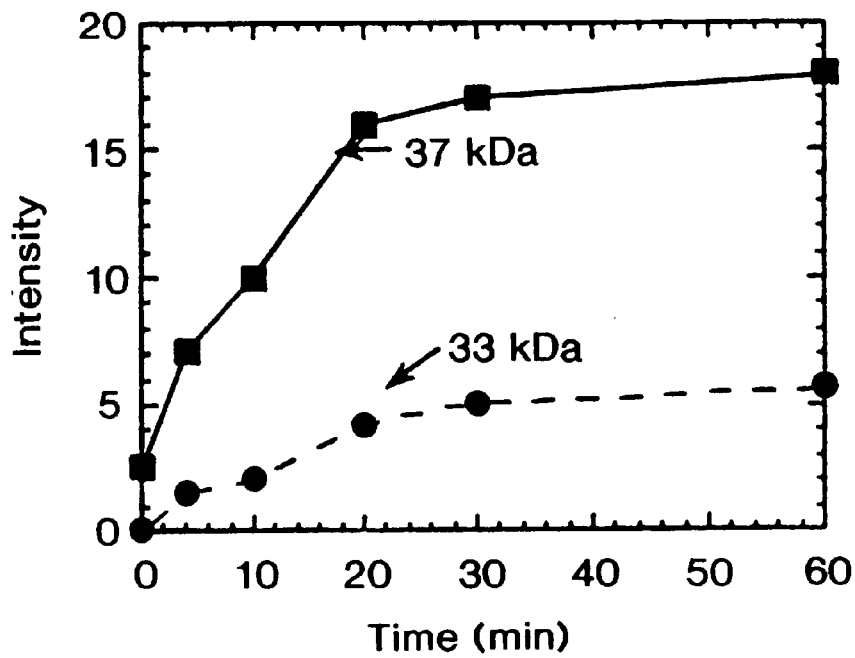

The fractionated membranes are incubated at 37° C. for times up to 4 hours to produce fragments of CD23 which are separated from the membrane after quenching the assay with 5 uM compound 1 by centrifugation at 10,000×g. These CD23 fragments are consistent with those reported (Letellier et al, J Exp. Med. 172, 693–700 (1990)): MW, app 36–37 kDa as determined by 12% sodium dodecylsulfate-polyacrylamide electrophoresis (SDS-PAGE) of N-terminal sequence QKSQ; MW, app 33 kDa with N-terminal sequence LKSQ. Additional bands not sequenced: MW, app 28–29 kDa and a doublet at 25–26 kDa. These are detected by Western blot of the total protein in the incubation using a polyclonal antibody such as the polyclonal anti-CD23 antibody in The Binding Site (Birmingham, UK) enzyme-linked immunoassay (EIA) Bindazyme kit for the determination of soluble CD23. Following removal of the membrane by centrifugation or filtration in 0.2 micron filter plates (Durapore, Millpore), sCD23 can also be determined using the EIA kit from The Binding Site or a similar one utilizing MHM6 anti-CD23 mAb (Rowe et al., Int. J. Cancer, 29, 373–382 (1982)) or another anti-CD23 mAb as the capture antibody in a sandwich EIA. As shown in FIG. 1, a typical time course is depicted for production of 37 and 33 kDa bands from plasma membrane enriched fractions from RPMI 8866 cells. Samples were incubated at 37° C. for the varying times, quenched with compound 1, applied to 12% SDS-PAGE, and Western blotting on PVDF (Bio-Rad) membrane performed using standard methodology with a combination of BD4 (prepared as described in Biological example 2) and a polyclonal antibody which recognizes all soluble fragments as the primary antibody. The blot was developed by ECL, scanned using a BioImage system and quantitated using the Visage analysis package.

Figure 2:
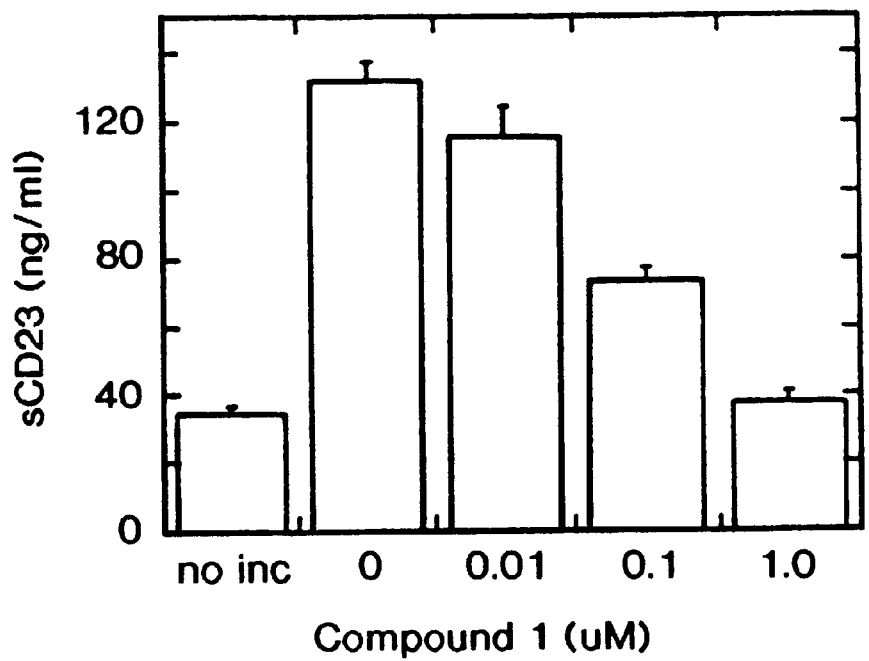

Inhibition of CD23 processing can also be determined by Western blot or by the 5 EIA (Elisa) method. The amount of soluble CD23 made by 0.5–5 ug membrane protein is measured either by quantitation of the Western blot as described using a Millipore BioImage system, or by EIA and compared to the amount made in the presence of various concentrations of inhibitors. Inhibitors are prepared in solutions of water or dimethylsulfoxide (DMSO) and the final DMSO concentration is not more than 2%. The enzyme activity of CD23 processing is inhibited by 1,10-phenanthroline (1 mM), and not by 1,7-phenanthroline (1 mM), PMSF (1 mM), E-64 (10 uM), pepstatin (10 uM), leupeptin (10 uM), or tosyl-leucylchloroketone (100 uM), and weakly by phosphoramidon (40% inhibition at 100 uM). The enzyme can heretofore best be described as a metalloprotease rather than a serine, cysteine or acid protease. CD23 processing is also inhibited by compound 1 as illustrated in FIG. 2 and described in Biological Example 2a.

Biological Example 2

Solubilized membrane protein CD23 processing enzyme assay:

Protease is solubilized from the enriched plasma membranes prepared as described in Example 1 by incubation at 4° C. with a detergent, such as Nonidet P-40, octyl glucoside or Triton X-100, at 10–50 times the CMC for the detergent, for example 0.1% Nonidet P-40 in phosphate-buffered saline. Insoluble material is removed by centrifugation and CD23 can be removed by immunoaffinity chromatography with MHM6 or other anti-CD23 mAb on Affi-gel 10 (Bio-Rad). CD23 purified by immunoaffinity chromatography and eluted by either 0.2 M Tris-glycine pH 2.3 or 3 M ammonium thiocyanate, pH 6.5 is then a substrate for the protease preparation in the following manner. Solubilized protease is incubated at 37° C. for up to 3 hours with 0.05–0.2 ug CD23 (100–400 nM) and the product of MW, app 33 kDa is detected by Western blot using a specific anti-serum (identified as BD4) which recognizes only this band relative to other CD23 derived proteins. The specific anti-serum is made by immunizing rabbits in a standard manner with the peptide NH$_2$LKSQDLELSC conjugated to maleimide-activated keyhole limpet hemocyanin (Pierce Chemical).

Use of The Binding Site polyclonal anti-CD23, (Birmingham, UK) as described for the membrane cleavage activity does not show significant amounts of other of the soluble CD23 fragments being formed. That is, once the enzyme and CD23 are in soluble form the major product formed from CD23 is the MW, app 33 kDa product. When cleavage occurs with enzyme and CD23 in the membrane, the MW, app 37 kDa product is the major product.

The CD23 purified by immunoaffinity chromatography using MHM6 or similar Ab produces less than 5% (the detection limit) of the amount of the product detected with the specific antiserum if incubated by itself in the absence of the solubilized protease compared with incubation with the protease preparation. CD23 co-solubilized in the solubilized protease preparation is also proteolyzed and accounts for less than 10% of the product observed.

When solubilized protease is added to the CD23, the MW, app 33 kDa product is made in a manner which is proportional to the amount of protein added as well as the amount of CD23 present. When appropriate amounts of the protease and the CD23 are present, the amount of product made is linear with time.

The protease is active at cleaving CD23 at pH over 6.5–7.0, with a pKa for the activity vs. pH profile of 7.3. As with the membrane assay, the activity is inhibited by 1,10-phenanthroline and not by the other protease inhibitors (E-64, PMSF, leupeptin, pepstatin, TLCK as for the membrane assay). Compounds 1 and 2 also inhibited the activity in this assay with IC50's of between 0.01 and 0.1, and 0.03 and 0.3 respectively at 100 nM CD23.

CD23 processing activity from other cell types in addition to RPMI 8866 can also be detected by this method. Enriched plasma membranes are collected in the same manner and proteins are solubilized with detergent. The solubilized proteins can be used to cleave added CD23 in the manner described. Solubilized membrane proteins from the B cell line BJAB (Menezes et al, Biomedicine, 22, 276 (1975)), which do not express CD23 on the plasma membrane, cleave CD23 to the MW, app 33 kDa band as detected by the BD4 anti-serum described above at a similar rate as RPMI 8866 solubilized cell membranes. The CD23 processing enzyme can be detected in the same manner using solubilized membrane proteins from monocytic cell lines such as U937 and THP1. The activity is not detected using solubilized membrane proteins from T cell lines such as Jurkat or H9. In all these 30 cases, cells are grown in the resting state in media and under conditions familiar to one skilled in the art.

Figure 3:
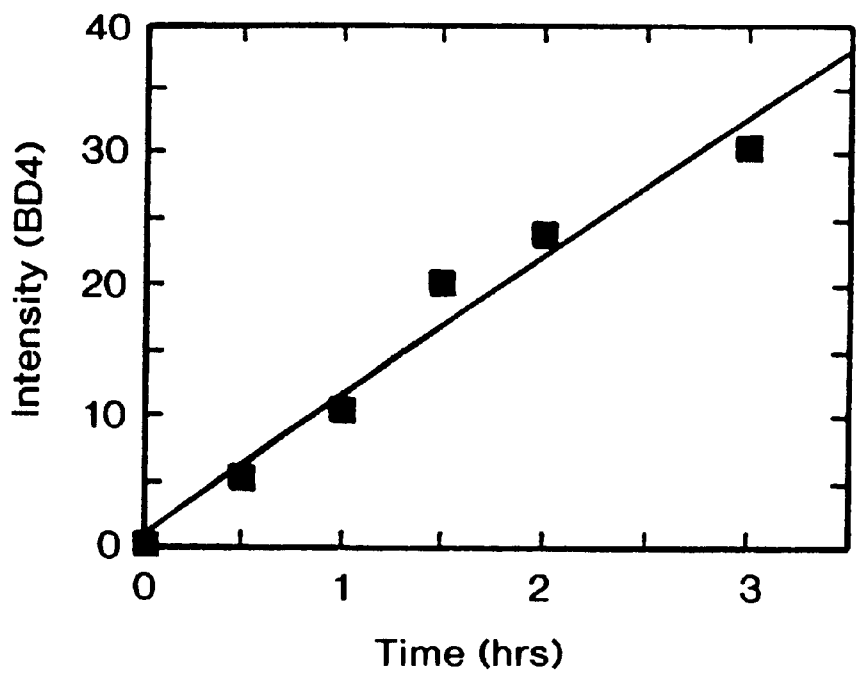

FIG. 3 describes a typical time course for cleavage of CD23 to MW, app 33 kDa fragment by solubilized RPMI 8866 membrane proteins. 0.7 ug solubilized membranes proteins were incubated with 110 nM CD23 for varying times, quenched in SDS-PAGE sample buffer and immediately boiled. Samples were applied to 12% SDS-PAGE, and Western blotting on PVDF membranes was performed using BD4 as the primary antibody, using standard methodology. The blot was quantitated as described above in FIG. 1. A straight line was fit to the plotted points.

Figure 4:
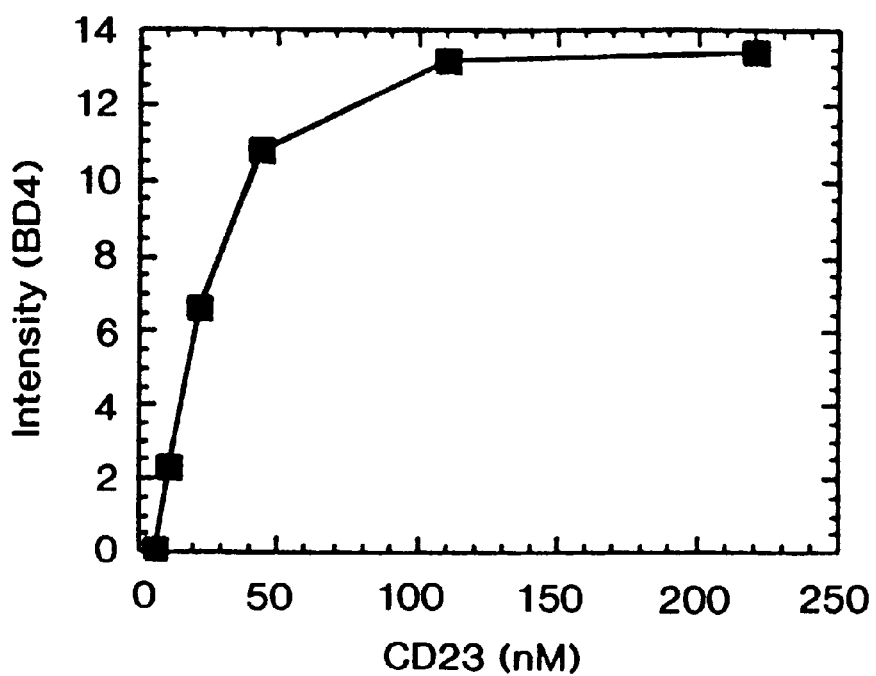

In FIG. 4 the dependence on CD23 concentration of production of 33 kDa sCD23 by solubilized plasma membrane proteins is shown. 0.7 ug of solubilized membrane proteins were incubated with varying amounts of CD23 for 2 hours at 37° C. in phosphate-buffered saline. Samples were quenched with SDS-PAGE sample buffer and analyzed as described above in FIG. 3. $K_M$, app is estimated to be between 20 and 40 nM CD23.

Biological Example 2a

Identification of inhibitors of CD23 processing enzyme

The assays described in Biological Examples 1 and 2 can be used to identify inhibitors of CD23 processing in a number of ways. Inhibitors of the membrane assay using membranes from RMPI 8866 are identified as follows. Membranes prepared as described in Example 1 are incubated in the absence or presence of inhibitor (as described in biological example 1) and the amount of soluble fragments determined either by Western blot or by EIA. The antibody used as the primary antibody in the Western as well as either the capture or the sandwich antibody in the EIA can be one which recognizes an epitope common to all the CD23 fragments, such as MHM6, or can be selective for one of the fragments such as the antibody described in Biological example 2. In the case of the selective antibody, no removal of unprocessed CD23 is required for detection of the products.

The enzyme activity is also inhibited by compounds 1 and 2, as described herein in the Synthetic Examples section, with IC50's of 0.1+/−0.05 and 2+/−1 uM respectively. IC50's are determined by curve fitting as the concentration where 50% inhibition of production of sCD23 is observed relative to sCD23 in a control incubated without inhibitor minus sCD23 in a control incubated with 5 uM compound 1. FIG. 2 demonstrates the dose dependent inhibition of the release of sCD23 from plasma membrane enriched fractions of RPMI 8866 cells by compound 1, as defined above. sCD23 was determined using the Binding Site Bindazyme kit in samples prepared as described in biological example 1, incubated with varying concentrations of compound 1. The IC50 was determined as described in example 1, 'no inc' refers to the control incubated with 5 uM compound 1.

The soluble assay in biological example 2 can also be used to identify inhibitors of CD23 processing. Solubilized membrane proteins from any cell type identified to have CD23 processing activity can be incubated with CD23 as substrate in the presence or absence of inhibitor. Specific cleavage of CD23 to 33 kDa fragment (the major product) can be determined by Western blot or by EIA using a selective Ab such as the one described in Biological example 2. For example, the assay can be quenched by addition of 5 uM compound 1, and samples analyzed by EIA using MHM6 as the capture antibody and a selective antibody used as the sandwich antibody. This assay would be familiar to one skilled in the art of EIA and would detect 33 kDa fragments without any removal of unprocessed CD23.

Biological Example 3

Heparin-agarose chromatography

Solubilized membrane proteins from RPMI 8866 cells are applied to heparin-agarose equilibrated in 50 mM HEPES, pH 7.5, 0.1% NP-40. Proteins are eluted with a gradient of 0 to 0.5 M NaCl in the same buffer and CD23 processing activity is observed at 0.2 M NaCl, when fractions are assayed by addition of CD23 to concentrated fractions as described in example 2.

Figure 5A:
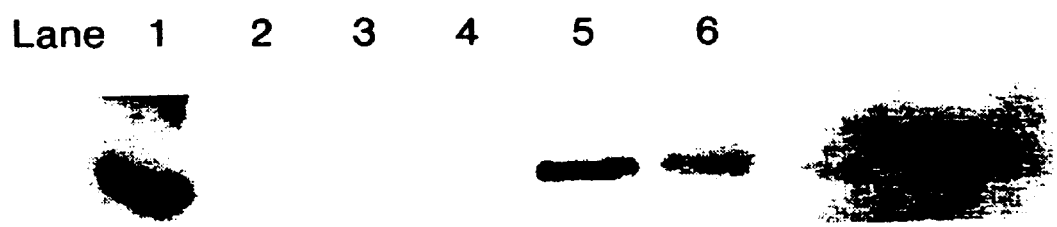
FIG. 5b depicts an elution profile of solubilized RPMI 8866 membrane proteins eluted from a heparin-agarose column.

FIG. 5a demonstrates the activity in the solubilized membrane protein assay by Western blot of fractions from the heparin-agarose column of solubilized RPMI 8866 membrane proteins. Fractions were concentrated in Millipore 10 concentrators, applied to 12% SDS-PAGE and Western blot performed as described in FIG. 3. This blot was scanned and quantitated as described in FIG. 3 to give the band intensity plotted in FIG. 5b. Lanes 5 and 6 correspond respectively to fractions 16 and 14 as shown in FIG. 5b, lanes 2–4 correspond to fractions 4, 10, and 12 in FIG. 5b, and lane 1 corresponds to material applied to the column (fraction 0).

Figure 5B:
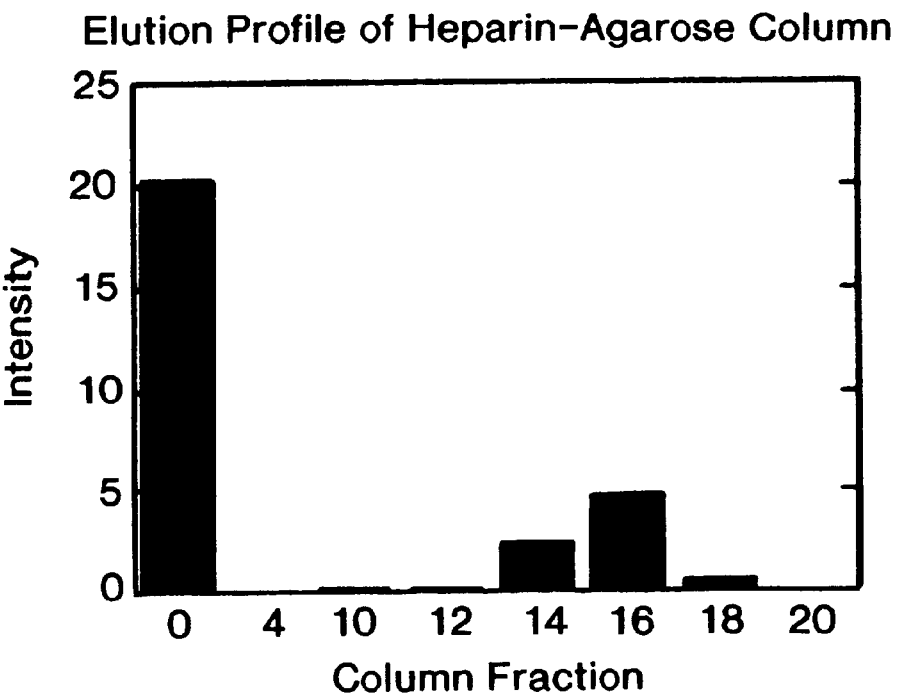

FIG. 5b therefore demonstrates the activity elution profile of solubilized RPMI 8866 membrane proteins eluted from a heparin-agarose column. Fractions were concentrated in Millipore 10 concentrators and incubated with CD23 as described, quenched and applied to 12% SDS-PAGE, and Western blot performed with BD4 as in FIG. 3. Fraction 0 corresponds to lane 1 in FIG. 5a, and fractions 4–16 correspond to 0.04 to 0.2 M NaCl in a linear gradient.

Biological Example 4

Q-Sepharose or Mono Q chromatography:

Solubilized protease is applied to Q-Sepharose resin or a Mono Q HR 5/5 column (Pharmacia) equilibrated in 50 mM HEPES pH 7.5 with 0.1% NP-40. Non-binding proteins are washed through in the same buffer and binding proteins are eluted with a gradient from 0 to 0.25 M NaCl. Fractions are assayed by addition of CD23 to concentrated fractions in the manner described in example 2 and activity is observed with a peak at 0.15–0.2 M NaCl.

Figure 6:
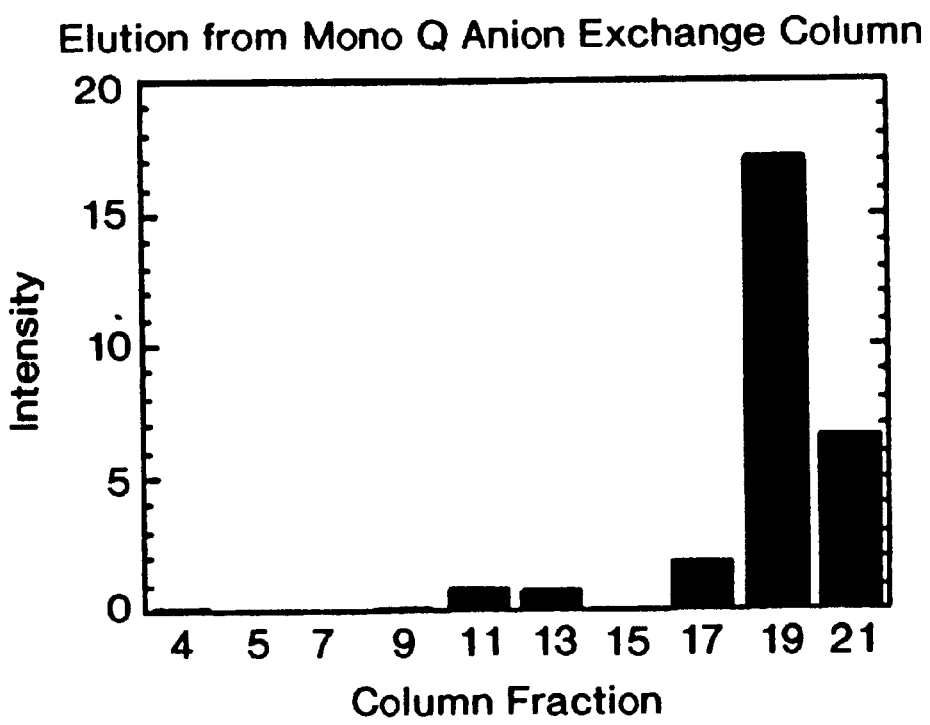
FIG. 6 depicts an elution profile of CD23 cleaving activity of fractions from a Mono Q HR 5/5 column with solubilized RPMI 8866 membrane proteins.

FIG. 6 demonstrates the elution profile of CD23 cleaving activity of fractions from a Mono Q HR 5/5 column with solubilized RPMI 8866 membrane proteins. Fractions were assayed as described in FIG. 5 and the activity quantitated as described in FIG. 3. Fractions 4–21 correspond to NaCl concentrations from 0.016 to 0.2 M in a linear gradient.

Biological Example 5

Mono S chromatography:

When solubilized protease is applied to a Mono S column in the same manner as the Mono Q, no activity which processes or cleaves CD23 in the manner described in example 2 is observed in the eluted fractions, but activity is found in the non-binding fractions.

Biological Example 6

Gel filtration chromatography

Solubilized protease is applied to Superose 12 (Pharmacia) equilibrated with 50 mM HEPES pH 7.5, 0.1% NP-40 and eluted at a flow rate of 0.3 m/min. The peak active fractions which process CD23 as described in example 2 correspond to a molecular weight of 45 to 60 kDa as determined by molecular weight standards.

Figure 7:
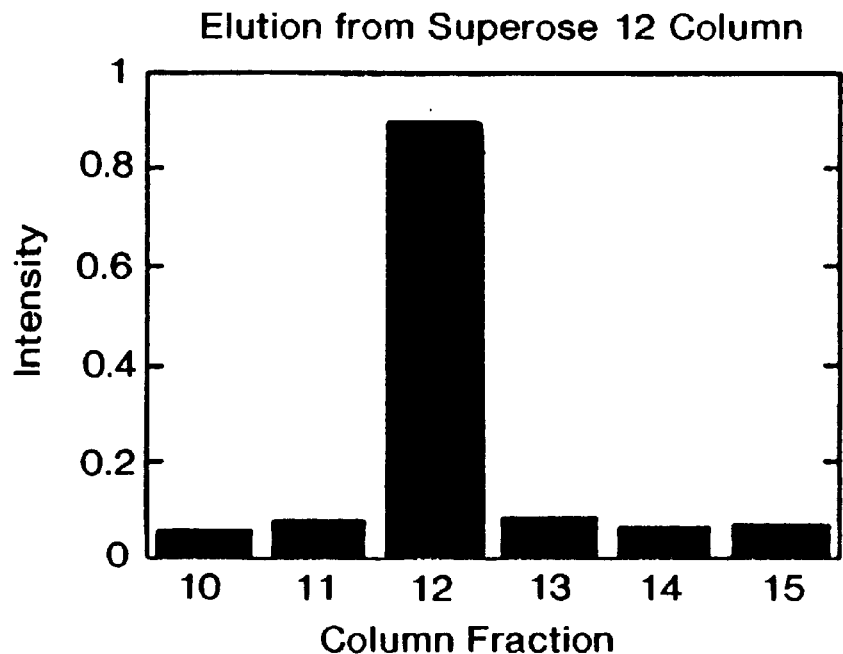
FIG. 7 depicts an elution profile of CD23 cleaving activity of fractions from a Superose 12 column with solubilized RPMI 8866 membrane proteins. Fractions were assayed as described in FIG. 5 and the activity quantitated as described in FIG. 3.

FIG. 7 demonstrates the elution profile of CD23 cleaving activity of fractions from a Superose 12 column with solubilized RPMI 8866 membrane proteins. Fractions were assayed as described in FIG. 5 and the activity quantitated as described in FIG. 3. The 45 kDa MW marker (Bio-Rad protein standards for gel filtration) co-elutes with fraction 12.

Biological Example 7

Photolabeling

Compound 3 is an inhibitor of CD23 processing in membranes with an IC50 of about 1–3 uM. Compound 3 (the synthesis of which is described in the Synthetic Examples section as Example 9), is [N-[4-N'-Hydroxyamino-2-(R)-2-(2-methylpropyl)succinyl]-S-4-azidophenylalanine-N"-(6-biotinoylaminohexyl)amide]. Compound 3 was prepared for use as a photolabeling agents as follows.

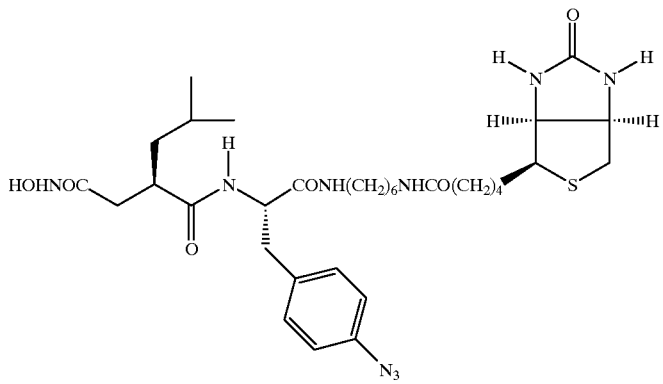

Column fractions from a Superose 12 column of solubilized membrane proteins from BJAB cells were photolabeled with 1 uM compound 3 using a Sunlit phosphor lamp at long UV for 1 min. A single band of MW, app 45 kDa as determined by SDS-PAGE is observed, as described in FIG. 8, under these conditions and only the active fractions as detected using the assay described in example 2 shows the photolabeled band. Active fractions from RPMI 8866 fractionations are similarly photolabeled.

FIG. 8 demonstrates the photolabeling with compound 3 of fractions from Superose 12 column of solubilized BJAB membrane proteins. Fractions were concentrated, photolabeled as described, applied to 12% SDS-PAGE, blotted to PVDF and photolabeled material detected with streptavidin-horseradish peroxidase (streptavidin-HRP) using ECL (Amersham) methodology. Fraction "0" indicates the photolabeling observed in an unfractionated sample. The 45 kDa MW marker protein migrated with an elution volume corresponding to fractions 17 or 18. The fraction sizes are not the same as FIG. 7.

Compound 4 (Synthetic Example 17), Compound 5 (Synthetic Example 17a), Compound 6 (Synthetic Example 25), and Compound 7 (Synthetic Example 27) can also be used to photolabel membranes or solubilized membrane proteins containing the CD23 processing enzyme, using the same method described for compound 3. Analysis by 12% SDS-PAGE and ECL detection of biotinylated protein, using streptavidin-HRP detects several bands in the molecular weight range 50–65 kDa.

More detailed analysis of the proteins labelled by compounds 3 and 4 was done by 2-dimensional gel electrophoresis (Pharmacia Multiphor II Dry Strip Kit, electrophoresis performed according to the manufacturer's instructions), and showed that there are several minor spots labeled by both compounds in addition to a large spot identified as adventitious biotinylation of actin. Up to 200 ug of membrane proteins in PBS were solubilized in 0.1 % NP-40 and photolabeled with 0.1 to 0.3 uM compound 4 or 1 uM compound 3 as described for compound 3 above. The sample was then dialyzed vs. 10 mM potassium phosphate pH 7.5, 0.1% NP-40, concentrated in a Centricon 10 (Amicon, Beverly Mass.), then made 8 M in urea, 2% in Triton X-100, 0. 8% in Pharmalyte 3–10 (Pharmacia) and 50 mM in DTT. After electrophoresis in both dimensions, the proteins were blotted to PVDF, and biotinylated proteins detected with streptavidin-HRP as described above. The majority of the minor biotinylated spots observed were in the molecular weight range 50–65 kDa and were acidic proteins with pH in the range 4.5–6.0.

Biological Example 8
Metal affinity chromatography

Solubilized membrane proteins from RPMI 8866 cells are applied to zinc-chelating Sepharose (Pharmacia) charged with Zn according to the manufacturer's instructions. CD23 processing activity is eluted from the resin with 0.1 M imidazole in 50 mM HEPES, pH 7.5, with 0.1% NP-40, as detected using the method described above in biological example 2.

FIG. 9 demonstrates an elution profile of RPMI 8866 membrane proteins from Zn-chelating Sepharose. Fractions were concentrated, assayed and activity quantitated as described in FIGS. 5 and 3.

Biological example 9
Dye column chromatography

Solubilized membrane proteins prepared as in example 2 can be applied to various dye resins. The following dye resins obtained from Sigma Chemical Co. (St. Louis, Mo.) have been tested for binding of CD23 cleaving activity, with results as tabulated below.

| | |
|---|---|
| red 120 | binds strongly, not eluted at 0.5 M NaCl in 50 mM HEPES, pH 7.5, 0.1% NP-40 (elution buffer) |
| yellow 86 | does not bind |
| green | binds, elutes with elution buffer |
| blue 14 | binds, elutes with elution buffer |
| blue 3GA | binds very weakly, elutes with high volume of buffer without NaCl |
| brown 10 | binds, elutes with elution buffer |

Biological Example 10
Affinity Chromatography with compound 8 (compound 28 in synthetic examples)

An affinity column was prepared with compound 8 on streptavidin-agarose beads (Pierce Chemical Co.) by overnight mixing of an estimated five equivalents of compound 8 with beads in 50 mM HEPES, pH 7.5, 0. 1% NP-40 (binding buffer). The column was washed with 20 volumes of this buffer and 20 volumes of 50 mM HEPES pH 7.5, 0.5% NP-40 in a syringe column, and re-equilibrated to binding buffer. An equivalent column with no compound 8 was also prepared. 150 ug of solubilized membranes from RPMI 8866 cells were applied to the both columns, washed with 3 ml binding buffer, 3 ml binding buffer with 0.1 M NaCl, and 3 ml binding buffer with 50 uM compound 2. Each 1 ml fraction was concentrated, diluted 10-fold and reconcentrated if compound 2 was present, and assayed as in biological example 2. For the column with no compound 8, CD23 processing activity was detected primarily in fractions 1–3, with a small amount in fractions 5 and 6. For the column with compound 8, activity was detected only in fractions 7–9. As compound 8 is an inhibitor of CD23 cleavage activity determined as in biological example 1, the activity is specifically bound to the affinity column and specifically eluted with another, weaker inhibitor of the enzymatic activity, added at a concentration of at least 10-fold higher than its $IC_{50}$, i.e. in excess.

Synthetic Examples

The invention will now be described by reference to the following examples which are merely illustrative and are not to be construed as a limitation of the scope of the present invention. In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Preparation of Compound 1: [4-(N-Hydroxyamino)-2-(R)-isobutyl-3-(S)-(2-thiophenethiomethyl)succinyl]-(S)-phenylalanine-N-methylamide, sodium salt

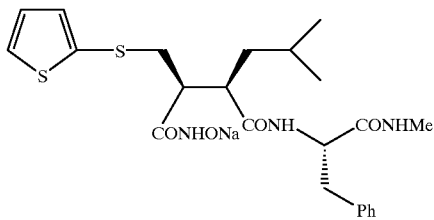

(P1)

This is prepared according to the procedure disclosed in WO 90/05719 (see example 11, the free acid being prepared in example 2) whose disclosure is incorporated herein by reference in its entirety.

Preparation of Compound 2: N-[3-(Hydroxycarboxamido)-2R-(2-methylpropyl)propanoyl-(S)-phenylalanine-N-benzylamide

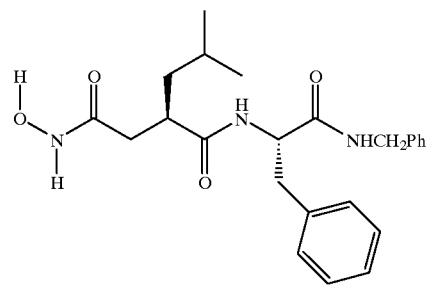

This compound is prepared from the precursor carboxylic acid and O-trimethylsilylhydroxylamine using similar methodology to that described in WO 90/05719 example 1 (g), whose disclosure is incorporated herein by reference in its entirety, but with bromo-tris-pyrrolidino-phosphonium hexafluorophosphate replacing water soluble carbodiimide as coupling agent.

Preparation of Compound 3: N-$^t$Butyloxycarbonyl-N'-biotinoylhexane-1,6-diamine

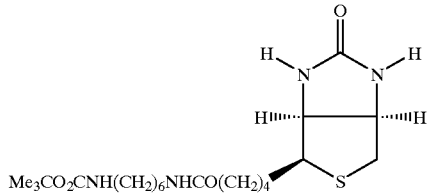

A mixture of N-$^t$butyloxycarbonylhexane-1,6-diamine (121 milligrams (hereinafter mg), 0.56 millimoles (hereinafter mmol)) and N-hydroxysuccinimidobiotin (NHS-biotin, Pierce), (94 mg, 0.275 mmol) in dry dimethylformamide (DMF) (5 milliliters (hereinafter ml)) was stirred at ambient temperature for about 2 hours (hereinafter h). The solvent was removed at reduced pressure and the residue partitioned between chloroform and water. The aqueous layer was extracted with chloroform (×2) and the combined organic layers were washed sequentially with 1M hydrochloric acid and saturated sodium bicarbonate then dried ($MgSO_4$), filtered and evaporated to give the title compound as a white solid (108 mg, 89%).

$MH^+$443; $MNa^+$465; $^1$H NMR (270 MHz; $d_6$ DMSO) 1.37 (9H, s); 1.13–1.57 (14H, m); 2.03 (2H, t, J=7.1 Hz); 2.57 (1H, d, J=12.3 Hz), 2.78–2.99 (3H, m); 3.01–3.07 (2H, m); 3.08–3.13 (1H, m); 4.10–4.14 (1H, m); 4.28–4.32 (1H, m); 6.35 (1H, s); 6.42 (1H, s); 6.76 (1H, t, broad); 7.72 (1H, t, J=5.2 Hz).

Preparation of Compound 4: N-Biotinoylhexane-1,6-diamine, trifluoroacetate salt

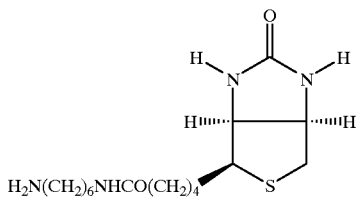

Trifluoroacetic acid (0.4 ml) was added to a suspension of N-tbutyloxycarbonyl-N'-biotinoylhexane-1,6-diamine (104 mg, 0.235 mmol) in chloroform (5 ml). The resulting solution was allowed to stand at ambient temperature for 45 minutes and then evaporated at reduced pressure. The resulting material was washed twice with toluene, the solvent evaporated and the residue left under high vacuum for 16 h at ambient temperature to give the title compound as a sticky gum in quantitative yield.

$MH^+$ (free base) 343; $MNa^+$365; $^1H$ NMR (270 MHz; $d_6$ DMSO) 1.16–1.62 (14H, m); 2.05 (2H, t, J=7.4 Hz); 2.57 (1H, d, J=12.4 Hz), 2.73–2.85 (3H, m); 2.99–3.12 (3H, m); 4.10–4.15 (1H, m); 4.29–4.33 (1H, m); 6.42 (2H, s, broad); 7.67 (3H, s, broad); 7.73 (1H, t, broad).

Preparation of Compound 5: N-'Butyloxycarbonyl-(S)-4-azidophenylalanine-N'-(6-biotinoylaminohexyl)amide

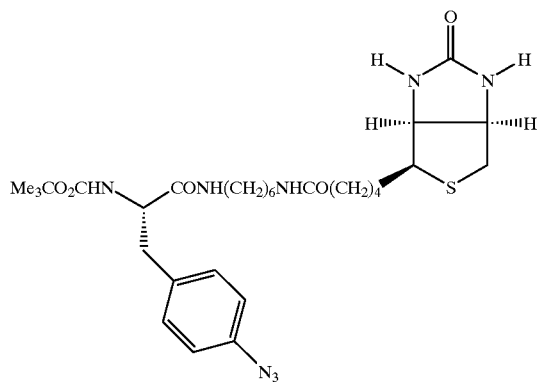

1-(3-Dimethylaminopropyl)-3-ethylcarbodiimide hydrochloride (DEC) (74 mg, 0.385 mmol) was added to a solution of N-tbutyloxycarbonyl-(S)-4-azidophenylalanine (100 mg, 0.327 mmol), N-biotinoylhexane-1,6-diamine, trifluoroacetate salt (148 mg, 0.324 mmol), 1-hydroxybenzotriazole (53 mg, 0.392 mmol) and diisopropylethylamine (51 mg, 0.395 mmol) in dry DMF (4 ml) under argon and the solution left to stir at ambient temperature for 24 h. The solvent was evaporated under reduced pressure and the residue washed with 10% citric acid, saturated sodium bicarbonate and water. The gummy solid was taken up in methanol and evaporated (×2), azeotroped with benzene and left under high vacuum for 2 days to remove final traces of water. Trituration with ethyl acetate gave the title compound as a white solid (100 mg, 49%).

$MH^+$631; $MNa^+$653; $^1H$ NMR (270 MHz; $d_6$ DMSO) 1.14–1.75 (14H, m); 1.30 (9H, s); 2.04 (2H, t, J=7 Hz); 2.59 (1H, d, J=12 Hz), 2.75–3.2 (8H, m); 4.0–4.2 (2H, m); 4.25–4.3 (1H, m); 6.35 (1H, s); 6.42 (1H, s); 6.9 (1H, d, J=7.5 Hz); 7.02 (2H, d, J=8.3 Hz); 7.27 (2H, d, J=8.3 Hz); 7.7 (1H, t, J=5 Hz); 7.8 (1H, t, broad).

Preparation of Compound 6: (S)-4-Azidophenylalanine-N-(6-biotinoylaminohexyl)-amide, trifluoroacetate salt

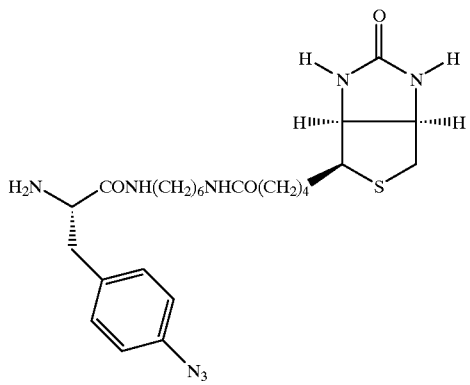

The title compound was prepared as a foam in quantitative yield from N-'butyloxycarbonyl-(S)-4-azidophenylalanine-N'-(6-biotinoylaminohexyl)amide (100 mg) and trifluoroacetic acid (0.4 ml) in chloroform (5 ml) using the procedure of Preparation 4.

$MH^+$ (free base) 530; $MNa^+$553; $^1H$ NMR (270 MHz; $d_6$ DMSO) 1.1–1.75 (14H, m); 2.04 (2H, t, J=7.1 Hz); 2.57 (1H, d, J=12.3 Hz), 2.75–2.80 (2H, m); 2.83–3.12 (6H, m); 3.9 (1H, m); 4.12–4.14 (1H, m); 4.28–4.33 (1H, m); 6.37 (1H, s); 6.41 (1H, s); 7.09 (2H, d, J=8.3 Hz); 7.25 (2H, d, J=8.3 Hz); 7.74 (1H, t, broad); 8.18 (3H, s); 8.28 (1H, t, J=5 Hz).

Preparation of Compound 7: N-[4-'Butyloxy-2-(R)-2-(2-methylpropyl)-succinyl]-S-4-azidophenylalanine-N'-(6-biotinoylaminohexyl)amide

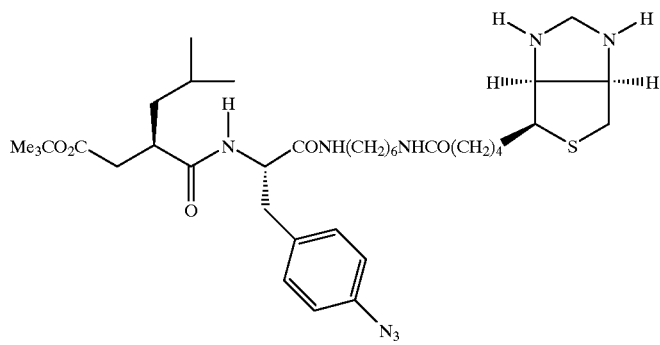

DEC (37 mg, 0.192 mmol) was added to a solution of (S)-4-azidophenylalanine-N-(6-biotinoylaminohexyl) amide, trifluoroacetate salt (103 mg, 0.160 mmol), 1-hydroxybenzotriazole (26 mg, 0.193 mmol), diisopropylethylamine (50 mg, 0.388 mmol) and 4-$^t$butyloxy-2R-2-(2-methylpropyl)succinic acid (37 mg, 0.161 mmol) in dry DMF (5 ml) under argon and the solution was allowed to stand for 23 h. The solvent was evaporated under reduced pressure and the resulting oil was triturated to a solid with ethyl acetate. The solid was washed with 10% citric acid (×2), saturated sodium bicarbonate (×2) and water (×2). Methanol was added and evaporated and the residue azeotroped with benzene (×2) to give the title compound as a solid (79 mg, 66%).

MH$^+$743; MNa$^+$765; $^1$H NMR (270 MHz; d$_6$ DMSO) 0.75 (3H, d, J=6.2 Hz); 0.82 (3H, d, J=6.2 Hz); 0.95–1.75 (17H, m); 1.34 (3H, s); 2.03 (2H, t, J=7 Hz); 2.1 (1H, dd); 2.25 (1H, dd); 2.5–3.2 (10H, m); 4.15 (1H, m); 4.3 (1H, m); 4.45 (1H, m); 6.4 (1H, s); 6.45 (1H, s); 6.99 (2H, d, J=8.4 Hz); 7.25 (2H, d, J=8.4 Hz); 7.7 (1H, t, broad); 7.8 (1H, t); 8.15 (1H, d).

Preparation of Compound 8: N-[4-Hydroxy-2-(R)-2-(2-methylpropyl)-succinyl]-S-4-azidophenylalanine-N'-(6-biotinoylaminohexyl)amide

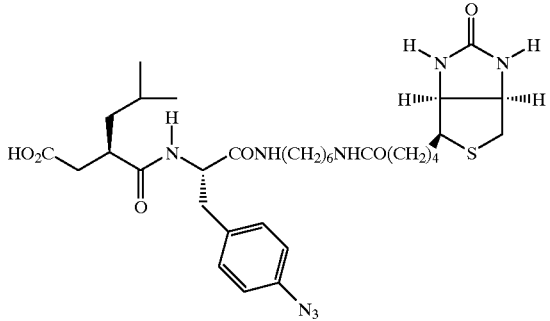

Trifluoroacetic acid (0.7 ml) was added to a suspension of N-[4-$^t$butyloxy-2-(R)-2-2-methylpropyl)succinyl]-S-4-azidophenylalanine-N'-(6-biotinoylamino-hexyl)amide (75 mg, 0.101 mmol in chloroform (3 ml)) and the resulting solution allowed to stir at ambient temperature for 5 h. The solvent was evaporated and the residue azeotroped with toluene (×2) to give the title compound as a solid (61 mg, 88%).

MNa$^+$709; $^1$H NMR (270 MHz; d$_6$ DMSO) 0.75 (3H, d, J=6 Hz); 0.82 (3H, d, J=6 Hz); 1.0–1.7(17H, m); 2.04(2H, t, J=7 Hz); 2.15(1H, dd); 2.3(1H, dd), 2.52(1H, d); 2.6(1H, m); 2.75–3.2 (8H, m); 4.15 (1H, m); 4.3 (1H, m); 4.45 (1H, m); 6.35 (1H, s); 6.45 (1H, s); 7.0 (2H, d, J=8.2 Hz); 7.2 (2H, d, J=8.2 Hz); 7.74 (2H, m); 8.07 (1H, d); 12.13 (1H, broad).

Preparation of Compound 9 (Compound 3 in text of specification): N-[4-N'-Hydroxyamino-2-(R)-2-(2-methylpropyl)succinyl]-S-4-azidophenylalanine-N"-(6-biotinoylaminohexyl)amide

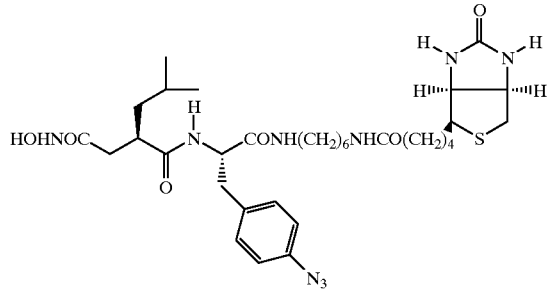

Isobutyl chloroformate (15 mg, 14 ul, 0.11 mmol) was added to a stirred solution of N-[4-hydroxy-2-(R)-2-(2-methylpropyl)succinyl]-S-4-azidophenylalanine-N'-(6-biotinoylaminohexyl)amide (57 mg, 0.083 mmol) and N-methylmorpholine (11 mg, 12 ul, 0.109 mmol) in dry DMF (2.5 ml) at −20° C. under argon. The solution was allowed to stir for 1 h at this temperature and then O-trimethylsilylhydroxylamine (70 mg, 0.666 mmol) added and the solution allowed to attain ambient temperature and left for 16 h. The solvent was evaporated under reduced pressure and the resulting solid washed with 10% citric acid (×2) and water (×2). Methanol was added and evaporated and the residue azeotroped with benzene. Trituration with ethyl acetate gave the title compound as an off-white solid (20 mg, 34%), mp 196–199° C. (MeOH/EtOAc.

IR(KBr disk) 3281,2931,2858,2117, 1710,1653, 1638cm$^{-1}$; MH$^+$702; MNa$^+$724. Accurate mass: MNa$^+$ Found 724.3583. C$_{33}$H$_{51}$N$_9$O$_6$SNa requires 724.3581; $^1$H NMR (400 MHz; d$_6$ DMSO) 0.73 (3H, d, J=6.4 Hz); 0.78 (3H, d, J=6.4 Hz); 0.93–1.00 (1H, m); 1.15–1.4 (12H, m); 1.4–1.55 (3H, m); 1.55–1.64 (1H, m); 1.89 (1H, dd, J=7.7, 14.3 Hz); 1.98–2.02 (1H, dd); 2.03 (2H, t, J=7.5 Hz); 2.57 (1H, d, J=12.5 Hz); 2.59–2.7 (1H, m), 2.76–2.83 (2H, m); 2.94–3.05 (5H, m); 3.06–3.11 (1H, m); 4.12 (1H, m); 4.31 (1H, m); 4.4 (1H, m); 6.34 (1H, s); 6.41 (1H, s); 7.0 (2H, d, J=8.4 Hz); 7.24 (2H, d, J=8.5 Hz); 7.71 (1H, t, J=5.5 Hz); 7.82 (1H, t, J=5.7 Hz); 8.04 (1H, d, J=8.5 Hz); 8.71 (1H, d, J=1.4 Hz); 10.36 (1H, d, J=1.4 Hz).

$^{13}$C NMR (400 MHz; d$_6$ DMSO); 2 methyl carbons 21.76, 23.2; 14 methylene carbons 25.24, 25.86, 26.01, 27.93, 28.10, 28.81, 29.02, 35.13, 35.57, 36.67, 38.2, 38.33, 39.66, 40.68, 10 methine carbons (2 identical) 25.06,40.28, 53.76, 55.31, 59.1, 60.95, 118.58 (×2), 130.61 (×2), 7 quaternary carbons 135.14, 137.09, 162.59, 167.40, 170.42, 171.67, 173.69.

Preparation of Compound 10: N-$^t$Butyloxycarbonyl-(S)-phenylalanine-N'-(6-biotinoylaminohexyl)amide

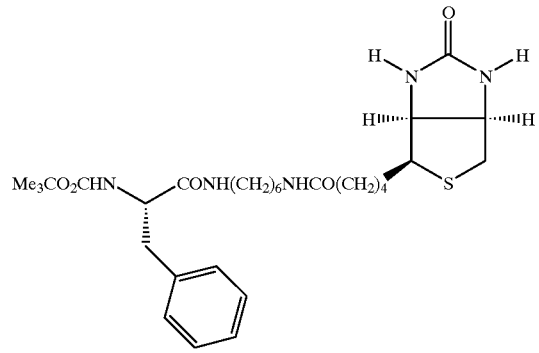

This material was prepared in 90% yield from N-tbutyloxycarbonyl-(S)-phenylalanine and N-biotinoylhexane-1,6-diamine, trifluoroacetate salt according to the procedure described for Compound 5 but replacing N-tbutyloxycarbonyl-(S)-4-azidophenylalanine by N-tbutyloxycarbonyl-(S)-phenylalanine.

MH$^+$590; MNa$^+$612; $^1$H NMR (270 MHz; d$_6$ DMSO) 1.22–1.75 (14H, m); 1.30 (9H, s); 2.04 (2H, t, J=7.3 Hz); 2.57 (1H, d, J=12.4 Hz), 2.78–3.09 (8H, m); 4.11–4.2 (2H, m); 4.28 (1H, m); 6.35 (1H, s); 6.43 (1H, s); 6.85 (1H, d, J=8.5 Hz); 7.17–7.3(5H, m); 7.7 (1H, t, J=5 Hz); 7.8 (1H, t, broad).

Preparation of Compound 11: (S)-Phenylalanine-N-(6-biotinoylaminohexyl)-amide, trifluoroacetate salt

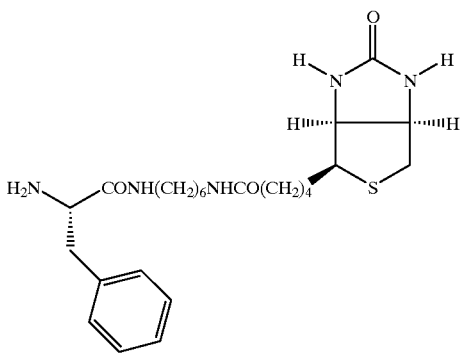

The title compound was prepared as a foam in 94% yield from N-tbutyloxycarbonyl-(S)-phenylalanine-N'-(6-biotinoylaminohexyl)amide (7.72 g) and trifluoroacetic acid (31 ml) in chloroform (300 ml) using the procedure described for Compound 4.

MH$^+$(free base) 490; MNa$^+$512; $^1$H NMR (270 MHz; d$_6$ DMSO) 1.06–1.75 (14H, m); 2.04 (2H, t, J=7.1 Hz); 2.57 (1H, d, J=12.3 Hz), 2.75–2.80 (2H, m); 2.83–3.12 (6H, m); 3.9 (1H, m); 4.12–4.14 (1H, m); 4.28–4.33 (1H, m); 6.37 (1H, s); 6.41 (1H, s); 7.19–7.22 (2H, m); 7.27–7.33 (3H, m); 7.75 (1H, t, broad); 8.20 (3H, s); 8.25 (1H, m).

Preparation of Compound 12: N-[4-$^t$Butyloxy-3-methylene-2-(R)-2-(2-methylpropyl)succinyl]-S-phenylalanine-N'-(6-biotinoylaminohexyl)amide

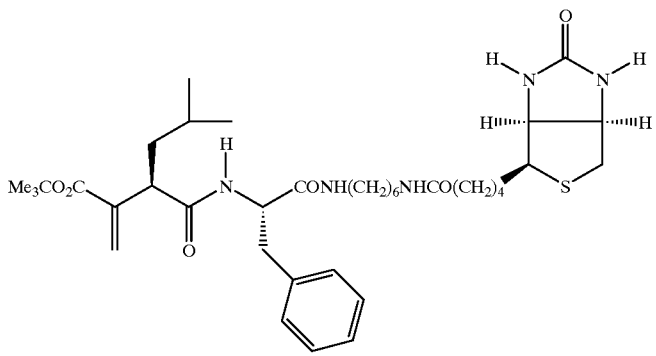

1-(3-Dimethylaminopropyl)-3-ethylcarbodiimide hydrochloride (DEC 1.0 g, 5.18 mmol) was added to a solution of (S)-phenylalanine-N-(6-biotinoylamino-hexyl)amide, trifluoroacetate salt (2.61 g, 4.33 mmol), 1-hydroxybenzotriazole (0.642 g, 4.76 mmol), diisopropylethylamine (1.12 g, 8.68 mmol) and 4-$^t$butyloxy-3-methylene-2R-2-(2-methylpropyl)succinic acid (1.15 g, 4.75 mmol) in dry DMF (36 ml) under argon and the solution was allowed to stand for 3 days. The solvent was evaporated under reduced pressure and the resulting oil was triturated to a solid with ethyl acetate. The solid was washed with 10% citric acid (×2), water (×2), saturated sodium bicarbonate (×2) and water (×2). The solid was filtered, washed with water, ether and dried to give the title compound as an off-white solid (2.898 g, 94%).

$^1$H NMR (270 MHz; d$_6$ DMSO) 0.78 (3H, d, J=6.3 Hz); 0.84 (3H, d, J=6.3 Hz); 0.95–1.75 (26H, m); 2.04 (2H, t, J=7 Hz); 2.6 (1H, d); 2.75–3.2 (8H, m); 3.4 (1H, m), 4.15 (1H, m); 4.3 (1H, m); 4.45 (1H, m); 5.41 (1H, s), 5.92 (1H, s), 6.4 (1H, s); 6.49 (1H, s); 7.16–7.3 (5H, m); 7.7 (1H, t, broad); 7.8 (1H, t); 7.9 (1H, d).

Preparation of Compound 13: N-[4-Hydroxy-3-methylene-2-(R)-2-(2-methylpropyl)succinyl]-S-phenylalanine-N'-(6-biotinoylaminohexyl)amide

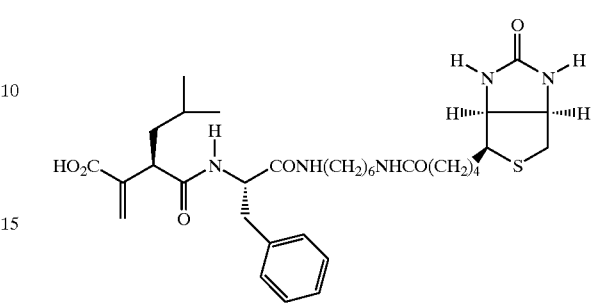

Trifluoroacetic acid (27.6 ml) was added to a suspension of N-[4-$^t$butyloxy-3-methylene-2-(R)-2-(2-methylpropyl)succinyl]-S-phenylalanine-N'-(6-biotinoylaminohexyl)amide (2.779 g, 3.89 mmol) in chloroform (118 ml) and the resulting solution allowed to stir at ambient temperature for 3 h. The solvent was evaporated and the residue azeotroped with toluene (×2) and triturated with ethyl acetate to give the title compound as an off-white solid (1.885 g, 74%).

$^1$H NMR (270 MHz; d$_6$ DMSO) 0.78 (3H, d, J=6.3 Hz); 0.83 (3H, d, J=6.3 Hz); 1.14–1.63 (17H, m); 2.04 (2H, t, J=7 Hz); 2.57 (1H, d, J=12.4 Hz); 2.73–3.12 (8H, m), 3.5 (1H, m); 4.15 (1H, m); 4.3 (1H, m); 4.45 (1H, m); 5.46 (1H, s), 6.00 (1H, s), 6.35 (1H, s); 6.43 (1H, s); 7.13–7.4 (5H, m) 7.72–7.77 (2H, m); 7.93 (1H, d, J=8.5 Hz); 12.6 (1H, broad).

Preparation of Compound 14: N-[4-Hydroxy-3-(S)-3-acetylthiomethyl-2-(R)-2-(2-methylpropyl)succinyl]-S-phenylalanine-N'-(6-biotinoylaminohexyl)amide

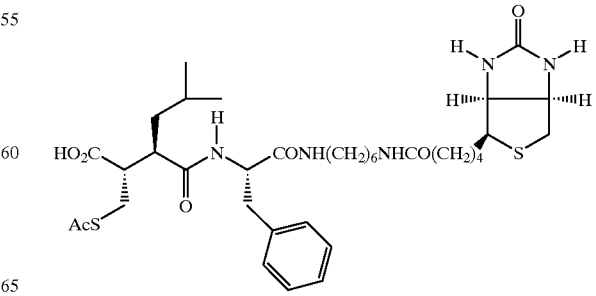

A mixture of N-[4-hydroxy-3-methylene-2-(R)-2-(2-methylpropyl)succinyl]-S-phenylalanine-N'-(6-biotinoylaminohexyl)amide (1.827 g, 2.78 mmol) and thiolacetic acid (23 ml) was stirred at ambient temperature for 20 h under argon. Evaporation of the solvent followed by trituration with ethyl acetate gave a solid which was filtered, washed with ethyl acetate, ether and dried to give the title compound as an off white solid (1.528 g, 75%).

¹H NMR (270 MHz; d₆ DMSO) 0.73 (3H, d, J=6.6 Hz); 0.80 (3H, d, J=6.6 Hz); 0.89–0.93 (1H, m), 1.2–1.62 (16H, m), 2.04 (2H, t, J=7 Hz); 2.26 (3H, s); 2.28–2.60 (4H, m), 2.75–3.13 (9H, m); 4.15 (1H, m); 4.3 (1H, m); 4.6 (1H, m); 6.35 (1H, s); 6.44 (1H, s); 7.13–7.4 (5H, m) 7.72 (1H, t); 7.83 (1H, t,); 8.38 (1H, d J=8.3 Hz), 12.4 (1H, broad).

solid was filtered, washed with water and dried to give the title compound (381 mg, 81%).

¹H NMR (270 MHz; d₆ DMSO) 0.73 (3H, d, J=6.6 Hz); 0.80 (3H, d, J=6.6 Hz); 0.89–0.93 (1H, m), 1.2–1.6 (16H, m), 1.6–1.76 (1H, m), 1.94 (1H, t, J=7.7 Hz), 2.04 (2H, t, J=7 Hz); 2.10–2.37 (3H, m); 2.57 (1H, d, J=12.4 Hz), 2.71–3.07 (8H, m), 4.13 (1H, m); 4.3 (1H, m); 4.59 (1H, m); 6.37 (1H, s); 6.45 (1H, s); 7.18–7.27 (5H, m) 7.72 (1H, t, J=5.5 Hz); 7.85 (1H, t,); 8.35 (1H, d J=8.5 Hz), 12.4 (1H, broad).

Preparation of Compound 16: N-[4-Hydroxy-3-(S)-3-(4-azidophenacylthiomethyl)-2-(R)-2-(2-methylpropyl)succinyl]-S-phenylalanine-N'-(6-biotinoylaminohexyl)amide

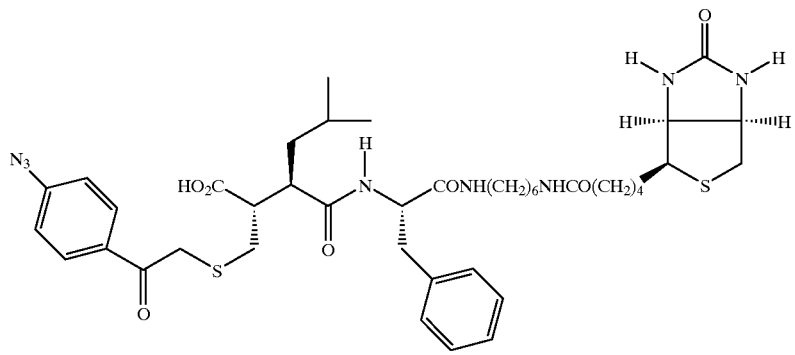

Preparation of Compound 15: N-[4Hydroxy-3-(S)-3-mercaptomethyl-2-(R)-2-(2-methylpropyl)succinyl]-S-phenylalanine-N'-(6-biotinoylaminohexyl)amide

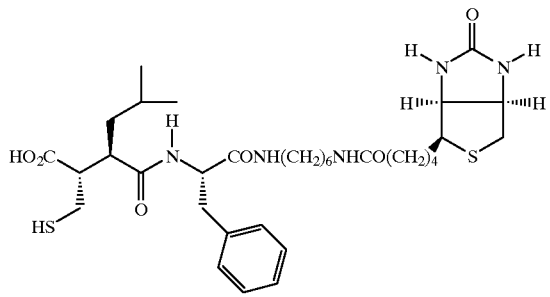

Sodium hydroxide solution (1M, 1.36 ml, 2 equivalents) was added to a solution of N-[4-hydroxy-3-(S)-3-acetylthiomethyl-2-(R)-2-(2-methylpropyl)succinyl]-S-phenylalanine-N'-(6-biotinoylaminohexyl)amide (500 mg) in methanol (20 ml) and left to stir at ambient temperature for 2 h under argon. Hydrochloric acid (1M) was added until pH ~3, the methanol evaporated and water added. The white Sodium hydroxide solution (1M, 460 ul, 2 equivalents) was added to a solution of N-[4-hydroxy-3-(S)-3-mercaptomethyl-2-(R)-2-(2-methylpropyl)succinyl]-S-phenylalanine-N'-(6-biotinoylaminohexyl)amide (160 mg, 0.23 mmol) and 4-azidophenacyl bromide (56 mg, 0.233 mmol) in methanol (30 ml) at room temperature under argon and the solution stirred for 2 h. Hydrochloric acid (1M) was added until pH -4, the methanol evaporated and water added to give a white solid. This was filtered, washed with water and dried to give the title compound (152 mg, 77%).

M Na⁺873; ¹H NMR (400 MHz; d₆ DMSO) 0.73 (3H, d, J=6.6 Hz); 0.79 (3H, d, J 6.6 Hz); 0.86–0.93 (1H, m), 1.10–1.2 (4H, m), 1.25–1.39 (8H, m), 1.4–1.55 (4H, m), 1.6 (1H, m), 2.04 (2H, t, J=7 Hz); 2.45 (1H, t, J=12 Hz), 2.45 (1H, dt), 2.58 (1H, d J=12.4 Hz), 2.74–2.84 (2H, m), 2.89–2.94 (1H, m), 2.95–3.02 (5H, m), 3.06–3.11 (1H, m), 3.76 (1H, d, J=14.7 Hz), 3.88 (1H, d, J=14.7 Hz), 4.11–4.13 (1H, m), 4.28–4.31 (1H, m), 4.51–4.57 (1H, m), 6.3–6.5 (2H, br), 7.05 (1H, t, J=7.1 Hz), 7.17–7.28 (6H, m), 7.70 (1H, t, J=5.5 Hz), 7.81 (1H, t, J=5.6 Hz), 7.96 (2H, d, J=8.7 Hz), 8.3 (1H, d, J=8.6 Hz), 12.4 (1H, broad).

Preparation of Compound 17: N-[4-N' Hydroxyamino-3-(S)-3-[(2-[4-azidophenyl]-2-[hydroxyimino]ethyl)-thiomethyl]-2-(R)-2-(2-methylpropyl)succinyl]-S-phenylalanine-N'-(6biotinoylaminohexyl)amide

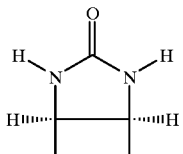
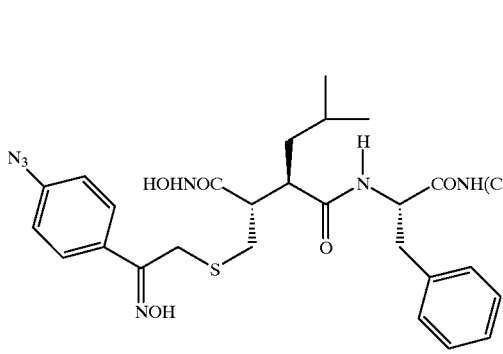

A solution of 1-hydroxy-7-azabenzotriazole (HOAt, 10.4 mg, 0.074 mmol), DEC (15 mg, 0.078 mmol) and N-[4-hydroxy-3-(S)-3-(4-azidophenacylthiomethyl)-2-(R)-2-(2-methylpropyl)succinyl]-S-phenylalanine-N'-(6-biotinoylaminohexyl)amide (50 mg, 0.059 mmol) in DMF (0.4 ml) was stirred at ambient temperature for 2 h under argon. Hydroxylamine hydrochloride (33 mg, 0.47 mmol) and N-methylmorpholine (52 ul) were then added and the solution was stirred for 16 h. The DMF was evaporated, water added and the solid filtered. The material was washed with water and ether and dried to give the title compound as a white solid (43 mg, 84%),as a 74:26 mixture of oxime isomers, mp 183–6°.

IR (KBr) 3287, 2932, 2866, 2129, 2099, 1685, 1653, 1635 cm$^{-1}$. MH$^+$ found 881.4170. $C_{42}H_{60}N_{10}O_7S_2H^+$ requires 881.4166. $^1$H NMR (400 MHz; d$_6$ DMSO) peaks quoted for major isomer only 0.73 (3H, d, J=6.6 Hz); 0.79 (3H, d, J=6.6 Hz); 0.86–0.93 (1H, m), 1.10–1.2 (4H, m), 1.25–1.39 (8H, m), 1.4–1.55 (4H, m), 1.6 (1H, m), 1.85–1.89 (1H, m), 2.04 (2H, t, J=7 Hz); 2.12–2.5 (3H, m,), 2.58 (1H, d J=12.4 Hz), 2.74–2.94 (1H, m), 2.95–3.02 (5H, m), 3.06–3.11 (1H, m), 3.53 (1H, d, J=11.9 Hz), 3.57 (1H, d, J=11.9 Hz), 4.11–4.13 (1H, m), 4.28–4.31 (1H, m), 4.51–4.57 (1H, m), 6.34 (1H, s), –6.42 (1H, s), 7.07–7.14 (3H, m,), 7.19–7.26 (4H, m), 7.65 (2H, d, J=8.7 Hz), 7.69–7.95 (2H, m), 8.27 (1H, d, J=8.4 Hz), 8.86 (1H, s), 10.54 (1H, s), 11.51 (1H, s).

$^1$H NMR (400 MHz; d$_6$ DMSO) peaks quoted for major isomer only 2 methyl carbons 21.39 and 24.02; 15 methylene carbons 24.20, 25.24, 25.24, 25.87, 26.03, 27.93, 28.09, 28.86, 29.03, 32.98, 35.13, 37.42, 38.20, 38.28, 39.86; 16 methine carbons (2 identical) 24.99, 46.06,46.25, 53.87, 55.30, 59.10, 60.95, 118.43, 118.99, 128.22, 127.36, 127.82, 128.98, 130.21;9 quaternary carbons 131.75, 137.70, 139.61, 151.93, 162.61, 168.28, 170.51, 171.67, 172.48.

Preparation of Compound 17a: N-[4-Hydroxyamino-3-(S)-3-(4-azidophenacylthiomethyl)-2-(R)-2-(2-methylpropyl) succinyl]-S-phenylalanine-N'-(6-biotinoylaminohexyl) amide The titled compound may be prepared in accordance with the procedures noted above for Preparation of Compound 17 except using 1 equivalent of hydroxylamine hydrochloride and 1 equivalent of N-methylmorpholine accordingly.

Preparation of compound 18:N-tertButyloxycarbonyl-(S)-tert-leucine-N'-(6-biotinoylaminohexyl)amide

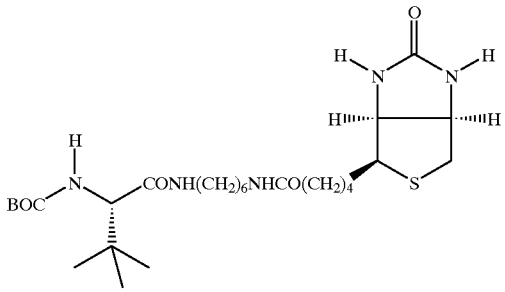

Compound 4 (1 g, 2.2 mmol), N-tert-Butyloxycarbonyl-(S)-tert-leucine(0.5 g, 2.2 mmol), and HOBt (354 mg, 2.62 mmol) were dissolved in DMF then diisopropylethylamine (0.59 ml, 4.2 mmol) and DEC (505 mg, 2.62 mmol) added. After stirring at ambient temperature for 10 h the solvent was removed under reduced pressure and the residue washed with 10% citric acid, sodium bicarbonate solution (×2) and water. Drying under vacuum gave the title compound as a white solid (1.126 g, 93%).

MH$^+$556; MNa$^+$578; $^1$ H NMR (270 MHz; d$_6$ DMSO) 0.89 (9H, s); 1.2–1.65 (14H, m); 1.38 (9H, s); 2.04 (2H, t, J=7 Hz); 2.55–2.8 (2H, m); 3.00 (3H, q, J=6 Hz), 3.05–3.22 (2H, m); 3.59 (1H, d, J=8 Hz); 4.08–4.15 (1H, m); 4.60 (1H, t, J=4.5 Hz); 6.35 (1H, s); 6.43 (1H, s); 7.42 (1H, t, J=8 Hz), 7.54 (1H, t, J=8 Hz); 7.85 (1H, br).

Preparation of compound 19: (S)-tert-leucine-N-(6-biotinoylaminohexyl)amide, trifluoroacetate salt

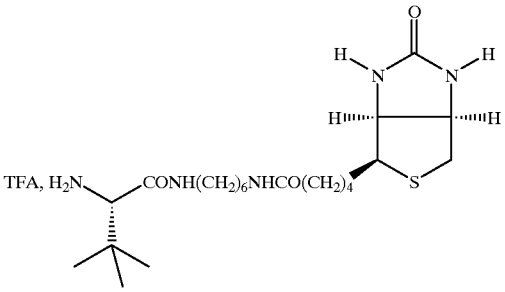

The title compound was prepared as a white solid from N-tert-Butyloxycarbonyl-(S)-tert-leucine-N'-(6-biotinoylaminohexyl)amide (1.1 g, 2 mmol) and trifluoroacetic acid (3 ml) in chloroform (50 ml) using the procedure of the titled compound.

MH+456; MNa+478 $^1$H NMR (270 MHz; d$_6$ DMSO) 0.96 (9H, s); 1.16–1.62 (14H, m); 2.05 (2H, t, J=7 Hz); 2.55–2.8 (2H, m); 3.00 (3H, q, J=6 Hz);3.2–3.3 (3H, m); 4.10–4.15 (1H, m); 4.29–4.35 (1H, m); 6.38 (1H, br); 6.42 (1H, br); 7.75 (1H, br); 8.05 (3H, br); 8.35 (1H, t, br).

Preparation of compound 20: Dimethyl-2S-Hydroxy-3R-(4-nitrobenzyl)succinate

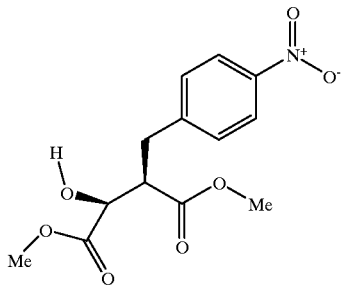

To a solution of diisopropylamine (9.1 ml, 69.4 mmol) in tetrahydrofuran (75 ml) at −10° C. was added dropwise n-butyllithium (1.6M in hexanes, 43.4 ml, 69.4 mmol). The reaction was stirred for 30 min then cooled to −70° C. and a solution of 2-(S)-dimethyl malate (5.116 g, 31.6 mmol) in tetrahydrofuran (10 ml) was added dropwise. After a further 30 min 4-nitrobenzyl bromide (8.64 g, 40 mmol) in tetrahydrofuran (25 ml) was added dropwise and the solution was stirred for 3 h before being poured into 2N hydrochloric acid and extracted with diethyl ether (×3). The extracts were dried (MgSO$_4$) and the solvent removed under reduced pressure. The residue was chromatographed (ethyl acetate/hexane) to give the product as a yellow solid (3.17 g, 34%).

MH+288; $^1$H NMR (270 MHz; CDCl$_3$) 3.06–3.35 (4H, m); 3.69 (3H, s); 3.79 (3H, s); 4.10 (1H, dd, J=5,2 Hz); 7.45 (2H, d, J=6.5 Hz); 8.19 (2H, d, J=6.5 Hz).

Preparation of compound 21: Dimethyl-2S-Hydroxy-3R-(4-aminobenzyl)succinate

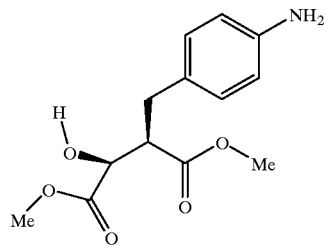

To dimethyl-2S-hydroxy-3R-(4-nitrobenzyl)succinate (3.74 g, 12.6 mmol) in methanol was added 10% palladium on carbon (400 mg) and the resultant suspension was hydrogenated at 35 psi for 30 min. The catalyst was removed by filtration through celite and the solvent removed under reduced pressure to give the title compound as a pale brown oil (3.33 g, 100%).

MH+268; MNH$_4$+285; $^1$H NMR (270 MHz; CDCl$_3$) 1.58 (2H ,br); 2.88 (1H, dd, J=15,4 Hz); 3.05–3.13 (3H, m); 3.68 (3H, s); 3.75 (3H, s); 4.11 (1H, app t, J=7 ); 6.65 (2H, d, J=8 Hz); 7.05 (2H, d, J=8 Hz).

Preparation of compound 22: Dimethyl-2S-Hydroxy-3R-(4-azidobenzyl)succinate

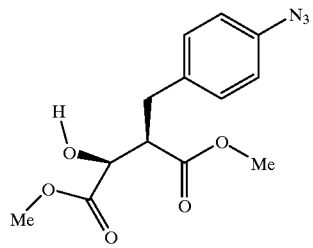

To a suspension of dimethyl-2S-hydroxy-3R-(4-aminobenzyl)succinate (3.3 g, 12.4 mmol) in water (80 ml) was added conc. sulphuric acid (2.37 ml, 44.6 mmol). The resultant solution was cooled to 0° C. and sodium nitrite (910 mg, 13.2 mmol) added portionwise. After 45 min sodium azide (910 mg, 14 mmol) in water (5 ml) was added and the solution allowed to warm to ambient temperature for 45 min before being extracted with dichloromethane (×3), dried (MgSO$_4$) and the solvent removed under reduced pressure.

MH+294; MNH$_4$+311; $^1$H NMR (270 MHz; CDCl$_3$) 2.97 (1H, dd, J=16, 12 Hz); 3.07–3.22 (3H, m); 3.68 (3H, s); 3.77 (3H, s); 4.08 (1H, br); 6.98 (2H, d, J=8.5 Hz); 7.25 (2H, d, J=8.5 Hz).

Preparation of compound 23: 2R-(2,2-Dimethyl-4-oxo-1,3-dioxalan-5S-yl)-3-(4-azidophenyl)propanoic acid

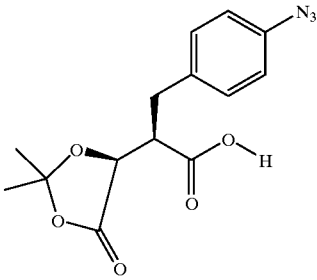

Dimethyl-2S-hydroxy-3R-(4-azidobenzyl)succinate was dissolved in 1,4-dioxan (50 ml) and potassium hydroxide (2.08 g, 37.2 mmol) in water (50 ml) added. The solution was refluxed for 3 h then cooled and acidified to pH ~2 using Dowex 50WX8-100 resin. The resin was removed by filtration, the solvent removed under reduced pressure and the residue azeotroped with toluene (×3). This material was then dissolved in tetrahydrofuran (15 ml) and 2,2-dimethoxypropane (100 ml) added followed by hydrochloric acid (1N in diethyl ether, 5 ml). The solution was then refluxed for 2 days, cooled and the solvent removed under reduced pressure. The residue was purified by chromatography (ethyl acetate/hexane) to give the title compound as a pale brown oil (2.964 g, 77%).

MH+306; MNH$_4$+323; $^1$H NMR (270 MHz; CDCl$_3$) 1.52 (3H, s); 1.61 (3H, s); 2.97 (1H, dd, J=12, 8 Hz); 3.14–3.32 (2H, m); 4.29 (1H, d, J=3 Hz); 6.98 (2H, d, J=8.5 Hz); 7.24 (2H, d, J=8.5 Hz) (carboxylic acid H not observed).

Preparation of compound 24: N'-[2R-(2,2-Dimethyl-4-oxo-1,3-dioxalan-5S-yl)-3-(4-azidophenyl)propanoyl]-S-tert-leucine-N-(6-biotinoylaminohexyl)amide

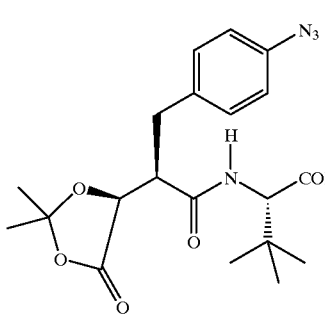

2R-(2,2-Dimethyl-4-oxo-1,3-dioxalan-5S-yl)-3-(4-azidophenyl)propanoic acid (134 mg, 0.44 mmol), HOBt (72 mg, 0.53 mmol) and DEC (102 mg, 0.53 mmol) were stirred in dry DMF (5 ml) for 20 mins then treated with (S)-tert-leucine-N-(6-biotinoyl-aminohexyl)-amide, trifluoroacetate salt (250 mg, 0.44 mmol) and diisopropyl-ethylamine (0.15 ml, 0.88 mmol). The solution was stirred at ambient temperature for 16 h then the solvent was removed under reduced pressure and the residue washed with 10% citric acid (×2), 10% sodium bicarbonate (×2), water (×2) and diethyl ether (×3) to give a pink solid as a 1:1 mixture of diastereoisomers (195 mg, 60%). MH 743;

Preparation of compound 25 (compound 6 in specification of text): N'-[3S-Hydroxy-4-(N-hydroxyamino)-2R-(4-azidobenzyl)succinyl]-S-tert-leucine-N-(6-biotinoylaminohexyl)amide

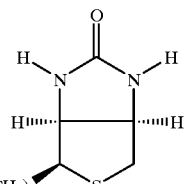

To N'-[2R-(2,2-Dimethyl-4-oxo-1,3-dioxalan-5S-yl)-3-(4-azidophenyl)propanoyl]-S-tert-leucine-N-(6-biotinoylaminohexyl)amide (90 mg, 0.12 mmol) in MeOH (3 ml) was added hydroxylamine hydrochloride (33 mg, 0.48 mmol) followed by N-methyl morpholine (52 ul, 0.48 mmol). The solution was stirred at ambient temperature for 3 days, then concentrated under reduced pressure and triturated with diethyl ether (×3) then water (×3). The residue was dried to give the title compound as a tan solid, as a 1:1 mixture of diastereoisomers (22 mg, 25%). MNa$^+$740.

Preparation of compound 26: N-[(3-(S)-(4-benzoylbenzyl)thiomethyl-2R-isobutyl)succinyl]-(S)-phenylalanine-N-(6-biotinoylaminohexyl)amide

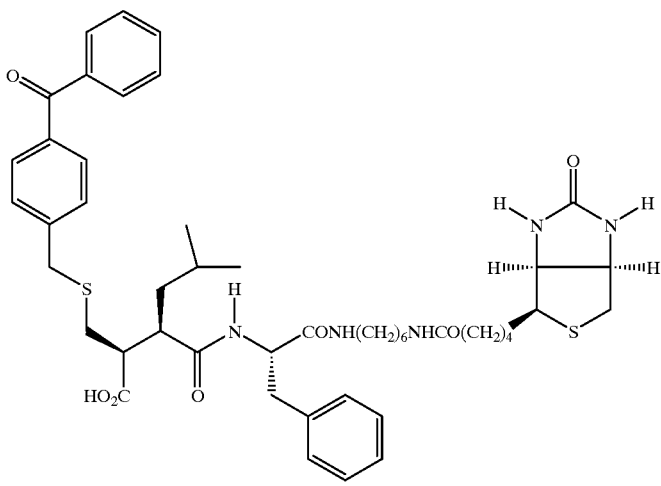

To a solution of compound 14 (200 mg, 0.27 mmol) and 4-benzoylbenzyl bromide (74 mg, 0.27 mmol) in MeOH (8 ml) was added 1N NaOH (0.82 ml, 0.82 mmol) giving a white precipitate which was stirred at ambient temperature for 3 days. The solvent was removed under reduced pressure, diluted with water and acidified to pH 2 with 2N HCl. The solid was removed by filtration, washed with water then diethyl ether and dried to give a white solid (165 mg, 68%).

MH$^+$886; MNH$_4^+$908; $^1$H NMR (270 MHz; d$_6$ DMSO), 0.72 (3H, d, J=6.5 Hz); 0.77 (3H, d, J=6.5 Hz); 1.0–1.75 (18H, m); 2.04 (2H, d, J=7 Hz); 2.3–2.55 (3H, obs); 2.75–3.15 (12H, m); 4.13 (1H, br); 4.30 (1H, app t, J=5 Hz); 4.50 (1H, m); 6.37 (1H, br);, 6.45 (1H, br); 7.11–7.31 (6H, m); 7.40 (2H, d, J=8.5 Hz); 7.56 (2H, d, J=8.5 Hz); 7.6–7.8 (5H, m); 7.92 (1H, br); 8.42 (1H, d, J=8 Hz).

Preparation of compound 27 (compound 7 in text of specification): N-[(3-(S)-(4-benzoylbenzyl)thiomethyl-4-(N-Hydroxyamino)-2R-isobutyl)succinyl]-(S)-phenylalanine-N-(6-biotinoylaminohexyl)amide Preparation of Compound 28 (compound 8 in text of specification): N-[(3-(S)-propargylthiomethyl-4-(N-Hydroxyamino)-2R-isobutyl)succinyl]-(S)-phenylalanine-N-(6-biotinoylaminohexyl)amide

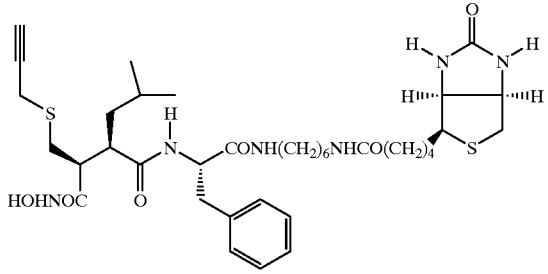

This compound was prepared in an analogous way to compound 27, from compound 14 (153 mg, 0.21 mmol) and propargyl bromide (31 mg, 80% solution in toluene, 0.21

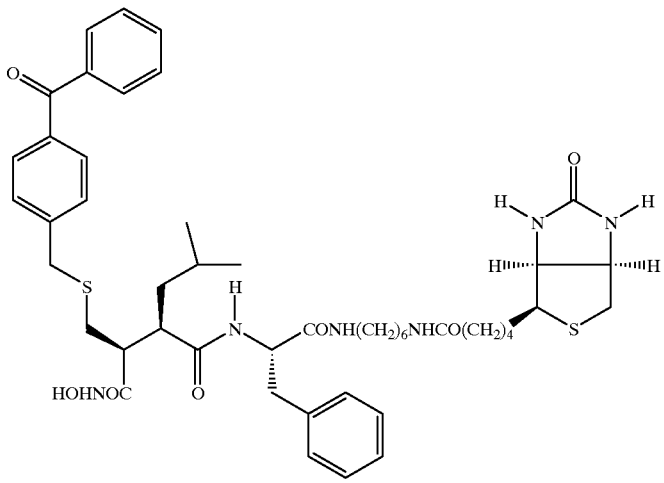

A solution of N-[(3-(S)-(4-benzoylbenzyl)thiomethyl-2R-isobutyl)succinyl]-(S)-phenylalanine-N-(6-biotinoylaminohexyl)amide (145 mg, 0.164 mmol), HOAt (29.2 mg, 0.215 mmol) and DEC (41.3 mg, 0.215 mmol) in dry DMF (5 ml) was stirred for 1 h then hydroxylamine hydrochloride (14.9 mg, 0.215 mmol) and N-methyl morpholine (24 ul, 0.215 mol) added. The solution was stirred for18 h at ambient temperature. The solvent was evaporated under reduced pressure and the residue washed with 10% citric acid, saturated sodium bicarbonate solution and water. After drying, concentration gave a white solid (96 mg, 65%).

MH$^+$901; MNH$_4^+$918; $^1$H NMR (400 MHz; d$_6$ DMSO), 0.72 (3H, d, J=6.5 Hz); 0.77 (3H, d, J=6.5 Hz); 1.0–1.75 (18H, m); 2.04 (2H, d, J=7 Hz); 2.18–2.35 (2H, m); 2.41 (1H, t, J=8.5 Hz); 2.58 (1H, d, J=12.5 Hz); 2.75–3.15 (10H, m); 3.55 (1H, dd, J=53, 13 Hz); 4.13 (1H, br); 4.30 (1H, app t, J=5 Hz); 4.50 (1H, m); 6.37 (1H, br);, 6.45 (1H, br); 7.11–7.31 (6H, m); 7.40 (2H, d, J=8.5 Hz); 7.56 (2H, d, J=8.5 Hz); 7.6–7.8 (5H, m); 8.38 (1H, d, J=8 Hz); 8.89 (1H, s); 10.6(1H, s).

mmol) followed by a DEC coupling with hydroxylamine to give the product as a white solid (60 mg, 38% from thioacetyl compound).

MNa$^+$767; $^1$H NMR (270 MHz; d$_6$ DMSO), 0.72 (3H, d, J=6.5 Hz); 0.77 (3H, d, J=6.5 Hz); 1.0–1.75 (17H, m); 2.04 (2H, t, J=7 Hz); 2.18–2.35 (3H, m); 2.41–2.60 (4H, m); 2.75–3.15 (8H, m); 3.55 (1H, dd, J=53, 13 Hz); 4.13 (1H, br); 4.30 (1H, app t, J=5 Hz); 4.50 (1H, m); 6.37 (1H, br);, 6.45 (1H, br); 7.11–7.37 (5H, m); 7.6–7.78 (2H, m); 8.32 (1H, d, J=8 Hz); 8.87 (1H, s); 10.51 (1H, s).

While the present invention includes all of the above noted compounds, preferably those compounds are:

N-[(3-(S)-(4-benzoylbenzyl)thiomethyl-4-(N-Hydroxyamino)-2R-isobutyl)succinyl]-(S)-phenylalanine-N-(6-biotinoylaminohexyl)amide;

N-[(3-(S)-propargylthiomethyl-4-(N-Hydroxyamino)-2R-isobutyl)succinyl]-(S)-phenylalanine-N-(6-biotinoylaminohexyl)amide;

N-[4-N'-Hydroxyamino-2-(R)-2-(2-methylpropyl) succinyl]-S-4-azidophenylalanine-N"-(6-biotinoylaminohexyl)amide;

N-[4-Hydroxy-3-(S)-3-(4-azidophenacylthiomethyl)-2-(R)-2-(2-methylpropyl)succinyl]-S-phenylalanine-N'-(6-biotinoylaminohexyl)amide;

N-[4-N' Hydroxyamino-3-(S)-3-[(2-(4-azidophenyl]-2-[hydroxyiminolethyl)-thiomethyl]-2-(R)-2-(2-methylpropyl)succinyl]-S-phenylalanine-N'-(6-biotinoylaminohexyl)amide;

N'-[3S-Hydroxy-4-(N-hydroxyamino)-2R-(4-azidobenzyl) succinyl]-S-tert-leucine-N-(6-biotinoylaminohexyl) amide; or a pharmaceutically acceptable salt thereof.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

enzyme elutes at a salt concentration from about 0.15 to about 0.2M;

f) applying the active fractions from part (e) to a metal chelating column, and eluting the enzyme from the column with 0.1 M imidazole, which eluate has CD23 converting activity upon dilution of the imidazole; such that the enzyme is a zinc metalloprotease.

4. The process according to claim 3 wherein the gel filtration is performed on a Superose 12 column.

5. The process according to claim 3 wherein the immbolized heparin column is a heparin-agarose column.

6. The process according to claim 3 wherein the metal chelating column is a Zn-chelating Sepharose column.

7. A method of identifying inhibitors of the CD23 processing enzyme of claim 1 which method comprises:
   a) preparing enriched plasma membranes from cells expressing CD23;
   b) incubating the membranes in the presence of, and in the absence of suspected inhibitors; and

What is claimed is:

1. A membrane bound CD23 converting enzyme having the following properties:
   a) an enzyme activity which produces MW, about 37 and 33 kDa CD23 fragments in a membrane cleavage assay;
   b) the activity is inhibited by (4-(N-Hydroxyamino)-2-(R)-isobutyl-3-(S)-(2-thiophenethiomethyl)-succinyl)-(S)-phenylalanine-N-methylamide and 1,10-phenanthroline;
   c) the activity is not inhibited by the protease inhibitors E-64, PMSF, leupeptin, pepstatin, and TCLK in the membrane assay.

2. A CD23 converting enzyme according to claim 1 having a maximum activity at a pH of about 7.5.

3. A process for preparing the purified CD23 converting enzyme of claim 1 which process comprises:
   a) preparing purified plasma membranes by aqueous extraction;
   b) solubilizing the membrane proteins, from part (a), with a detergent;
   c) applying solubilized proteins, from part (b), to an anion exchange chromatography column and eluting the CD23 converting enzyme in the fractions eluting at a salt concentration from about 0.15 to about 0.25 M;
   d) passing the eluate, from part (c) through a column to obtain an eluate which has CD23 converting activity in the fractions with a MW between 45 and 60 kDa;
   e) applying the active fractions from part (d) to an immobilized heparin chromatography column and eluting the enzyme with a salt gradient, wherein the active c) determining the amount of sCD23 produced by the membrane incubation.

8. The method according to claim 7 wherein the method further comprises calculating the IC50 of the inhibitor by reference to uninhibited membrane cleavage activity.

9. The method according to claim 7 wherein the amount of sCD23 determined is the total amount of sCD23 produced.

10. The method according to claim 7 wherein the amount of sCD23 determined is by detection of sCD23 fragments of 33 kDa MW though use of selective antibodies.

11. A method of identifying inhibitors of the CD23 processing enzyme of claim 1 which method comprises:
   a) preparing enriched plasma membranes from cells expressing CD23;
   b) incubating the membranes in the presence of, and in the absence of suspected inhibitors; and
   c) determining the amount of 33 kDa CD23 produced.

12. The method according to claim 11 wherein the amount of CD23 produced is determined using a selective antibody to the 33 kDa fragment.

13. A method of identifying inhibitors of the CD23 processing enzyme of claim 1 which method comprises
   a) preparing enriched plasma membrane from cells expressing CD23;
   b) solubilizing the membranes in a detergent;
   c) adding a suitable amount of exogenous CD23 to the solubilized membrane protein;

d) incubating the mixture of part (c), in the presence of, and in the absence of an inhibitor;

e) detecting soluble fragments of CD23 or detecting the amount of unprocessed full length CD23.

14. The method according to claim 13 wherein the amount of sCD23 produced is determined using a selective antibody to the fragments.

15. The method according to claim 13 wherein the amount of unprocessed CD23 remaining is determined using a selective antibody to the full length CD23.

16. The method according to any of claim 13 wherein the exogenous CD23 is purified.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Human

<400> SEQUENCE: 1

Leu Lys Ser Gln Asp Leu Glu Leu Ser Cys
 1               5                  10